(12) United States Patent
Aggarwal et al.

(10) Patent No.: US 7,368,430 B2
(45) Date of Patent: May 6, 2008

(54) SELECTIVE INHIBITORS OF NUCLEAR FACTOR-κB ACTIVATION AND USES THEREOF

(75) Inventors: Bharat B. Aggarwal, Houston, TX (US); Sujay Singh, San Diego, CA (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 10/981,082

(22) Filed: Nov. 4, 2004

(65) Prior Publication Data

US 2005/0201976 A1 Sep. 15, 2005

Related U.S. Application Data

(60) Provisional application No. 60/517,852, filed on Nov. 6, 2003.

(51) Int. Cl.
*A61K 38/00* (2006.01)
(52) U.S. Cl. .................................................. 514/14
(58) Field of Classification Search .................... 514/14
See application file for complete search history.

(56) References Cited

U.S. PATENT DOCUMENTS 6,015,709 A * 1/2000 Natesan ...................... 435/366

OTHER PUBLICATIONS

Morris, MC, et al "A peptide carrier for the delivery of biologically active proteins into mammalian cells." Nat Biotechnol. Dec. 2001;19(12):1173-6.*
Pinilla C., et al, "Synthetic peptide combinatorial libraries (SPCLs): identification of the antigenic determinant of beta-endorphin recognized by monoclonal antibody 3E7," Gene, Jun. 15, 1993;128(1):71-6.*
Cardoso MC, et al "Protein transduction: a novel tool for tissue regeneration," Biol Chem. Oct. 2002;383(10):1593-9 From Applicant's Exhibit.*
Anrather et al., "Regulation of nk-kb rela phosphorylation and transcriptional activity by p21ras and protein kinase c in primary endothelial cells," *J. of Biol. Chem.*, 274:13594-13603, 1999.
Bohuslav et al., "p53 induces nf-kb activation by an Ikb kinase-independent mechanism involving phosphorylation of p65 by ribosomal s6 kinase 1," *J. of Biol. Chem*, 279, 26115-26125, 2004.
Buss et al., "Phosphorylation of serine 468 by gsk-3b negatively regulates basal p65 nf-kb activity," *J. of Biol. Chem*, 279:49571-49574, 2004.

Fujita et al., "Identification of nap1, a regulatory subunit of ikb kinase-related kinases that potentiates nf-kb signaling," *Molecular and Cellular Biology*, 23:7780-7793, 2003.
Mattioli et al., "Transient and selective nf-kb p65 serine 536 phosphorylation induced by t cell costimulation is mediated by ikb kinase b and controls the inetics of p65 nuclear import," *J. of Immunology*, 172:6336-6344, 2004.
O'Mahony et al., "Human t-cell lymphotropic virus type 1 tax induction of biologically active nf-kb requires ikb kinase-1-mediated phosphorylation of rela/p65," *J. of Biol. Chem*, 279: 18137-18145, 2004.
Schmitz et al., "Nf-kb: a multifaceted transcription factor regulated at several levels," *ChemBio Chem*, 5:1348-1358, 2004.
Vermeulen et al., "Transcriptional activation of the nf-kb p65 subunit by mitogen- and stress-activated protein kinase-1 (msk1)," *The Embo Journal*, 22:1313-1324, 2003.
Wang et al., "Tumor necrosis factor a-induced phosphyorylation of rela/p65 on ser529 in controlled by casein kinase ii," *J. of Biol. Chem*, 275:32592-32597, 2000.
Lindgren et al., "Cell-penetrating peptides," *TiPS*, 21:99-103, 2000.
Takada et al., "Identification of a p65 Peptide That Selectively Inhibits NF-kB Activation Induced by Various Inflammatory Stimuli and Its Role in Down-regulation of NF-kB-mediated Gene Expression and Up-regulation of Apoptosis," *J. Biol. Chem.*, 279:15096-15104, 2004.
Derossi et al., "The third helix of the Antennapedia homeodomain translocates through biological membranes," *J. Biol. Chem.*, 269:10444-10450, 1994.
Elliott and O'Hare, "Intercellular trafficking and protein delivery by a herpesvirus structural protein," *Cell*, 88:223-233, 1997.
Fawell et al., "Tat-mediated delivery of heterologous proteins into cells," *Proc. Natl. Acad. Sci. USA*, 91:664-668, 1994.
Schwarze and Dowdy, "In vivo protein transduction: intracellular delivery of biologically active proteins, compounds and DNA," *Trends Pharmacol. Sci.*, 21:45-48, 2000.

* cited by examiner

*Primary Examiner*—Cecilia J. Tsang
*Assistant Examiner*—Thomas S. Heard
(74) *Attorney, Agent, or Firm*—Fulbright & Jaworski LLP

(57) ABSTRACT

The present invention provides cell permeable NF-κB inhibitors consist of a polypeptide derived from the p65 subunit of NF-κB and a protein transduction domain derived from antennapedia third helix sequence. The inhibitor suppressed NF-κB activation induced by TNF, LPS, IL-1, okadaic acid, PMA, $H_2O_2$ and cigarette smoke condensate. NF-κB-regulated reporter gene expression induced by TNF, TNFR1, TRADD, TRAF2, NIK, IKK and p65 was suppressed by the inhibitor. The inhibitor enhanced TNF- and chemotherapeutic agent-induced apoptosis. Overall these results demonstrate a NF-κB inhibitor that can selectively inhibit NF-κB activation induced by various inflammatory stimuli, downregulate NF-κB mediated gene expression and upregulate apoptosis.

35 Claims, 17 Drawing Sheets

|  |  | SEQ ID NO. |
|---|---|---|
| DRQIK,IWFQN,NRRMK,WKK | PTD | 3 |
| DRQIK,IWFQN,NRRMK,WKK -QLRRP,SDREL,SE | PTD-p65-P1 | 4 |
| -QLRRP,SDREL,SE | p65-P1 | 5 |
| -QLRRP,ADREL,SE | p65-P2 | 6 |
| -QLRRP,ADREL,AE | p65-P3 | 7 |
| -QLRRP,SD | p65-P4 | 8 |
| -RP,SDREL,SE | p65-P5 | 9 |

|  |  | SEQ ID NO. |
|---|---|---|
| DRQIK,IWFQN,NRRMK,WKK -NGLLS,GDEDF,SS | PTD-p65-P6 | 10 |
| -NGLLS,GDEDF,SS | p65-P6 | 11 |
| -NGLLA,GDEDF,SS | p65-P7 | 12 |
| -NGLLS,GDEDF,SA | p65-P8 | 13 |

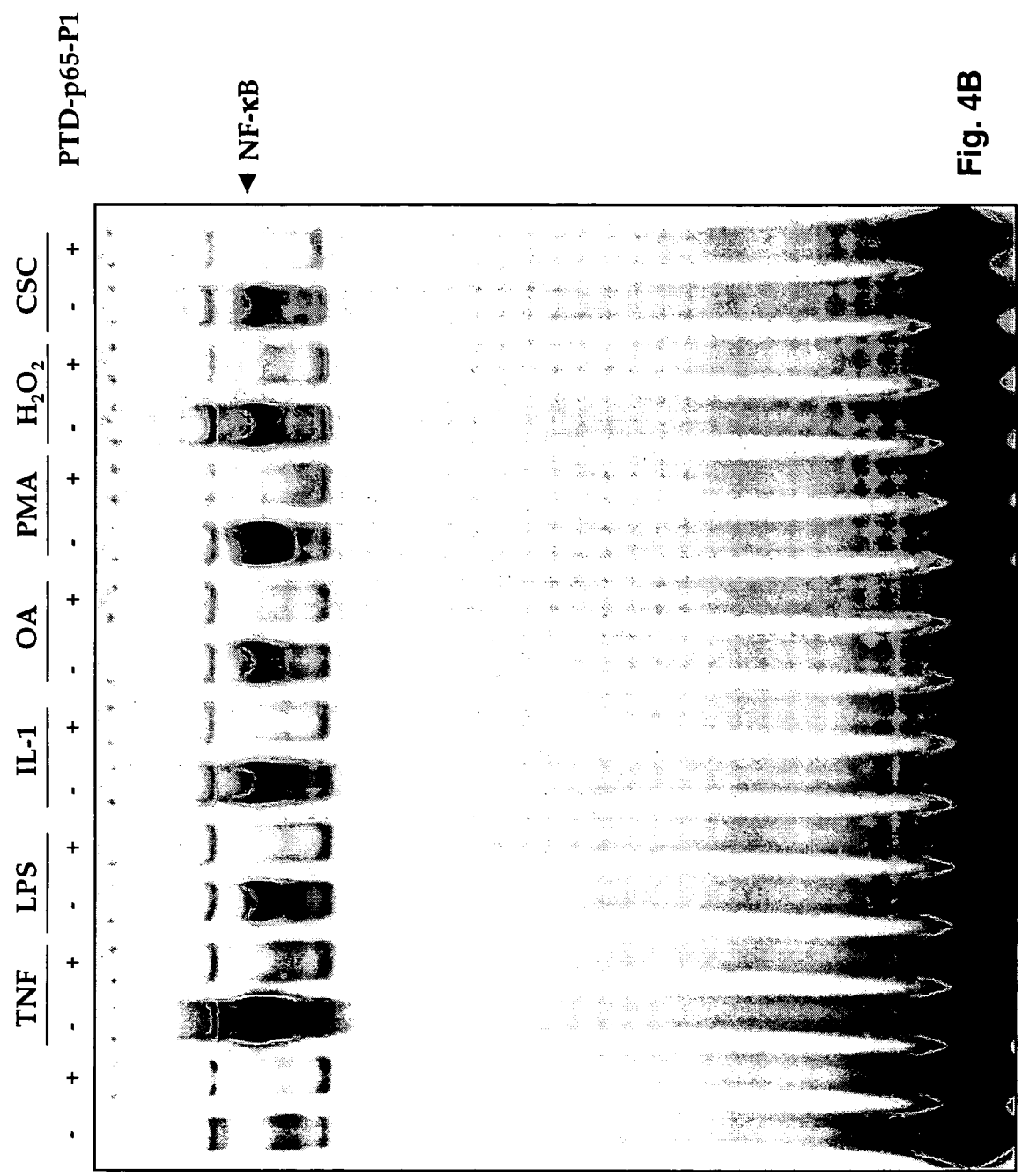

SEQUENCE LISTING

```
<160> NUMBER OF SEQ ID NOS: 13

<210> SEQ ID NO 1
<211> LENGTH: 45
<212> TYPE: DNA
<213> ORGANISM: Unknown
<220> FEATURE:
<221> NAME/KEY: protein_bind
<223> OTHER INFORMATION: oligonucleotide from the human immunodeficiency
      virus long terminal repeat containing
      NF-kB binding site

<400> SEQUENCE: 1
ttgttacaag gactttccg ctggggactt tccagggagg cgtgg            45

<210> SEQ ID NO 2
<211> LENGTH: 45
<212> TYPE: DNA
<213> ORGANISM: Unknown
<220> FEATURE:
<221> NAME/KEY: protein_bind
<223> OTHER INFORMATION: mutated oligonucleotide used to examine the
      specificity of DNA binding of NF-?B

<400> SEQUENCE: 2
ttgttacaac tcactttccg ctgctcactt tccagggagg cgtgg           45

<210> SEQ ID NO 3
<211> LENGTH: 18
<212> TYPE: PRT
<213> ORGANISM: Unknown
<220> FEATURE:
<221> NAME/KEY: CHAIN
<223> OTHER INFORMATION: protein transduction domain (PTD) derived from
      the third helix of the antennapedia homeodomain

<400> SEQUENCE: 3

Asp Arg Gln Ile Lys Ile Trp Phe Gln Asn Asn Arg Arg Met Lys
                 5                  10                  15
Trp Lys Lys

<210> SEQ ID NO 4
```

```
<211> LENGTH: 30
<212> TYPE: PRT
<213> ORGANISM: Unknown
<220> FEATURE:
<221> NAME/KEY: CHAIN
<223> OTHER INFORMATION: PTD-p65-P1, cell permeable NF-kb inhibitor

<400> SEQUENCE: 4

Asp Arg Gln Ile Lys Ile Trp Phe Gln Asn Asn Arg Arg Met Lys
                 5                  10                  15

Trp Lys Lys Gln Leu Arg Arg Pro Ser Asp Arg Glu Leu Ser Glu
             20                  25                  30

<210> SEQ ID NO 5
<211> LENGTH: 12
<212> TYPE: PRT
<213> ORGANISM: Unknown
<220> FEATURE:
<221> NAME/KEY: CHAIN
<222> LOCATION: 271 .. 282
<223> OTHER INFORMATION: p65-P1, peptide derived from the p65
      subunit of NF-kB

<400> SEQUENCE: 5

Gln Leu Arg Arg Pro Ser Asp Arg Glu Leu Ser Glu
                 5                  10

<210> SEQ ID NO 6
<211> LENGTH: 12
<212> TYPE: PRT
<213> ORGANISM: Unknown
<220> FEATURE:
<221> NAME/KEY: CHAIN
<223> OTHER INFORMATION: p65-P2, mutated peptide derived from the
      p65 subunit of NF-kB

<400> SEQUENCE: 6

Gln Leu Arg Arg Pro Ala Asp Arg Glu Leu Ser Glu
                 5                  10

<210> SEQ ID NO 7
<211> LENGTH: 12
<212> TYPE: PRT
<213> ORGANISM: Unknown
<220> FEATURE:
<221> NAME/KEY: CHAIN
<223> OTHER INFORMATION: p65-P3, mutated peptide derived from the
      p65 subunit of NF-kB

<400> SEQUENCE: 7

Gln Leu Arg Arg Pro Ala Asp Arg Glu Leu Ala Glu
                 5                  10

<210> SEQ ID NO 8
<211> LENGTH: 7
<212> TYPE: PRT
<213> ORGANISM: Unknown
<220> FEATURE:
<221> NAME/KEY: CHAIN
<223> OTHER INFORMATION: p65-P4, mutated peptide derived from the
      p65 subunit of NF-kB

<400> SEQUENCE: 8

Gln Leu Arg Arg Pro Ser Asp
                 5

<210> SEQ ID NO 9
<211> LENGTH: 9
```

```
<212> TYPE: PRT
<213> ORGANISM: Unknown
<220> FEATURE:
<221> NAME/KEY: CHAIN
<223> OTHER INFORMATION: p65-P5, mutated peptide derived from the
      p65 subunit of NF-kB

<400> SEQUENCE: 9

Arg Pro Ser Asp Arg Glu Leu Ser Glu
                 5

<210> SEQ ID NO 10
<211> LENGTH: 30
<212> TYPE: PRT
<213> ORGANISM: Unknown
<220> FEATURE:
<221> NAME/KEY: CHAIN
<223> OTHER INFORMATION: PTD-p65-P6, cell permeable NF-kb inhibitor

<400> SEQUENCE: 10

Asp Arg Gln Ile Lys Ile Trp Phe Gln Asn Asn Arg Arg Met Lys
                 5                   10                  15

Trp Lys Lys Asn Gly Leu Leu Ser Gly Asp Glu Asp Phe Ser Ser
                20                   25                  30

<210> SEQ ID NO 11
<211> LENGTH: 12
<212> TYPE: PRT
<213> ORGANISM: Unknown
<220> FEATURE:
<221> NAME/KEY: CHAIN
<223> OTHER INFORMATION: p65-P6, peptide derived from the p65 subunit
      of NF-kB

<400> SEQUENCE: 11

Asn Gly Leu Leu Ser Gly Asp Glu Asp Phe Ser Ser
                 5                   10

<210> SEQ ID NO 12
<211> LENGTH: 12
<212> TYPE: PRT
<213> ORGANISM: Unknown
<220> FEATURE:
<221> NAME/KEY: CHAIN
<223> OTHER INFORMATION: p65-P7, mutated peptide derived from the
      p65 subunit of NF-kB

<400> SEQUENCE: 12

Asn Gly Leu Leu Ala Gly Asp Glu Asp Phe Ser Ser
                 5                   10

<210> SEQ ID NO 13
<211> LENGTH: 12
<212> TYPE: PRT
<213> ORGANISM: Unknown
<220> FEATURE:
<221> NAME/KEY: CHAIN
<223> OTHER INFORMATION: p65-P8, mutated peptide derived from the
      p65 subunit of NF-kB

<400> SEQUENCE: 13

Asn Gly Leu Leu Ser Gly Asp Glu Asp Phe Ser Ala
                 5                   10
```

SELECTIVE INHIBITORS OF NUCLEAR FACTOR-κB ACTIVATION AND USES THEREOF

CROSS-REFERENCE TO RELATED APPLICATION

This patent application claims benefit of priority of provisional patent application U.S. Ser. No. 60/517,852, filed Nov. 6, 2003, now abandoned.

FEDERAL FUNDING LEGEND

This invention was produced in part using funds obtained through a Department of Defense US Army Breast Cancer Research Program grant (BC010610), a PO1 grant (CA91844) from the National Institutes of Health and a P50 Head and Neck SPORE grant from the National Institutes of Health. Consequently, the federal government has certain rights in this invention.

BACKGROUND OF THE INVENTION

1. Field of the Invention

The present invention relates generally to the molecular biology of nuclear factor-kappa B (NF-κB). More specifically, the present invention relates to polypeptides that can selectively inhibit NF-κB activation, downregulate NF-κB mediated gene expression and enhance apoptosis induced by TNF and other apoptotic stimuli.

2. Description of the Related Art

Nuclear Factor-κB (NF-κB) represents a group of five proteins, namely c-Rel, Rel A (p65), Rel B, NF-κB1 (p50 and p105), and NF-κB2 (p52). NF-κB is regulated by a family of inhibitors called IκB. In an inactive state, NF-κB is present in the cytoplasm as a heterotrimer consisting of p50, p65, and IκBα subunits. In response to an activation signal, the IκBα subunit is phosphorylated at serine residues 32 and 36, ubiquitinated at lysine residues 21 and 22, and degraded through the proteosomal pathway, thus exposing the nuclear localization signals on the p50-p65 heterodimer. The p65 is then phosphorylated, leading to nuclear translocation and binding to specific DNA sequence, which in turns results in transcription of various genes including cyclin D1, cyclooxyenase (COX) 2 and matrix metalloproteinase (MMP) 9.

The p65 subunit of NF-κB, which contains at least two strong transactivation domains (TAD) within the C terminus (TA1 30 amino acid; TA2 90 amino acid), has been shown to undergo phosphorylation upon activation. The sites of phosphorylation and the kinase responsible for p65 phosphorylation remain controversial. For instance, phosphorylation at Ser 276 by protein kinase A, at Ser 529 by casein kinase II, at Ser 536 by IKK-β, and at serine 471 by PKC-ε have been demonstrated. In addition, phosphorylation of p65-TAD by glycogen synthase kinase-3β and by $Ca^{2+}$/calmodulin-dependent protein kinase IV have been demonstrated.

NF-κB has been shown to regulate the expression of a number of genes whose products are involved in inflammation, viral replication, carcinogenesis, anti-apoptosis, invasion and metastasis. These include anti-apoptosis genes, adhesion molecules, chemokines, inflammatory cytokines, and cell cycle regulatory genes. Thus agents that can suppress NF-κB activation have the potential to treat a variety of diseases that involves inflammation, apoptosis and carcinogenesis.

Most proteins enter the cell through their specific cell surface receptors. Recent studies, however, indicate that certain short protein sequences can enter the cells without any receptors and such proteins have been described as protein transduction domain (PTD) peptides (Lindgren et al., 2000; Schwarze and Dowdy, 2000). Most of the protein transduction domain peptides are arginine-rich peptides (Futaki et al., 2003). Importantly, conjugation of proteins, peptides and antisense oligonucleotides to these protein transduction domain peptides has been shown to deliver these cargos effectively, allowing observation of biological action in several cell and animal models (Lindgren et al., 2000; Schwarze and Dowdy, 2000). Peptides derived from third helix of the antennapedia homeodomain, herpes virus structural protein, and HIV tat protein have been used to deliver both small and large peptides of interest to the cells through an energy- and receptor-independent mechanism (Derossi et al., 1994; Elliott and O'Hare, 1997; Fawell et al., 1994).

Using these protein transduction domain peptides, several peptides based on protein-protein interaction domains have been delivered to the cells to suppress cell signaling. These include Grb2 binding peptide, mitogen-activated protein kinase, STAT3, NEMO-IKK interacting peptide, and peptides carrying nuclear localization sequences. Besides peptides, protein transduction domain peptides have also been used to deliver larger full length polypeptides, including IκBα, cyclin-dependent kinase inhibitory protein p27, anti-apoptotic proteins Bcl-xl, and proapoptotic proteins.

The prior art is deficient in providing a cell permeable inhibitor specific for NF-κB. The present invention fulfills this long-standing need and desire in the art by disclosing the construction of a cell permeable NF-κB-specific inhibitor comprising a NF-κB polypeptide linked to an antennapedia-derived protein transduction domain. This inhibitor can suppress NF-κB activation, suppress NF-κB-mediated gene transcription and enhance apoptosis induced by TNF and other apoptotic stimuli.

SUMMARY OF THE INVENTION

The present invention is directed to a cell permeable NF-κKB inhibitor comprising (i) a polypeptide of SEQ ID NO. 5 or 11, or homologues or derivatives thereof, and (ii) a protein transduction domain which is able to transport the polypeptide across cell membrane. In general, the protein transduction domain is derived from the third helix of the antennapedia homeodomain, herpes virus structural protein, or HIV tat protein. In one embodiment of the present invention, the protein transduction domain derived from the third helix of the antennapedia homeodomain has the sequence of SEQ ID NO. 3, and the cell permeable NF-κB inhibitor has the sequences of SEQ ID NO. 4 or 10.

In another aspect, the present invention provides methods of using the NF-κB inhibitor to inhibit DNA binding activity of NF-κB or enhance apoptosis in a cell. In general, DNA binding activity of NF-κB induced by TNF, LPS, IL-1, okadaic acid, PMA, $H_2O_2$, cigarette smoke condensate, TNF receptor 1 (TNFR1), TNF receptor-associated death domain (TRADD), TNF receptor-associated factor 2 (TRAF2), NF-κB-inducing kinase (NIK), or IκBα kinase (IKK) could be inhibited by the inhibitor, whereas apoptosis induced by TNF, or chemotherapeutic agent such as doxorubicin or cisplatin could be enhanced by the inhibitor.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 1A show the p65 consists of a DNA-binding and dimerization domain (RHD), nuclear localization domain (NLS), and transactivation domain (TD). The p65 phosphorylation sites are indicated.

FIG. 1B shows the sequence of cell-permeable peptide and the p65 peptides. The protein transduction domain (PTD) sequence derived from antennapedia was conjugated with p65-P1 or p65-P6 for in vivo study. Other p65 peptides (p65-P1,-P8) without antennapedia segment were used for in vitro study.

FIG. 2A shows KBM-5 cells were treated with 0.1 nM TNF for 30 min, and the nuclear extracts were prepared, incubated for 30 min with various peptides, and then assayed for NF-κB activation by electrophoretic mobility shift assay (EMSA).

FIG. 2B shows dose-dependent effect of p65-P1 peptide on NF-κB binding to DNA in vitro. Nuclear extracts were prepared from TNF-treated cells, incubated for 30 min with various concentrations of peptides, and then assayed for NF-κB activation by EMSA.

FIG. 3A shows KBM-5 cells were incubated with 150 μM peptides for 1 h and treated with 0.1 nM TNF for the indicated times. Nuclear extracts were prepared, and then NF-κB activation was analyzed by EMSA.

FIG. 3B shows dose dependent effect. KBM-5 cells were incubated with various concentrations of peptides for 1 hour and treated with 0.1 nM TNF for 30 minutes. Nuclear extracts were prepared, and then NF-κB activation was analyzed by EMSA.

FIG. 3C shows PTD-p65-P6 peptide inhibits TNF-induced NF-κB activation. KBM-5 cells were incubated with various concentrations of peptides for 1 h and treated with 0.1 nM TNF for 30 min. Nuclear extracts were prepared, and then NF-κB activation was analyzed by EMSA.

FIG. 3D shows PTD-p65 peptides specifically inhibits TNF-induced NF-κB activation. KBM-5 cells were treated with 0.1 nM TNF for 30 min. Nuclear extracts were prepared, incubated for 30 min with different antibodies, preimmune serum (PIS), unlabeled NF-κKB oligo probes (Competitor), or mutant NF-κB oligo probe, and then assayed for NF-κB activation by EMSA.

FIGS. 4A-4B shows the effect of PTD-p65-P1 on TNF-induced AP-1 activity. FIG. 4A shows KBM-5 cells were incubated with various concentrations of peptides for 1 hour and treated with 0.1 nM TNF for 30 min. Nuclear extracts were prepared, and then NF-κB activation was analyzed by EMSA.

FIG. 4B shows PTD-p65-P1 peptide inhibits NF-κB activation induced by different activators. KBM-5 cells were incubated with 150 μM peptide for 1 h, treated with 0.1 nM TNF, 1 μg/ml LPS, 100 ng/ml IL-1, 500 nM okadaic acid (OA), 10 ng/ml PMA, 500 μM $H_2O_2$, or 1 μg/ml cigarette smoke condensate (CSC), and then analyzed for NF-κB by EMSA.

FIG. 5B shows PTD-p65-P1 peptide has no effect on the TNF-induced IKK activation. Cells were incubated with 150 μM PTD-p65-P1 for 1 h and treated with 0.1 nM TNF for the indicated times. Whole-cell extracts were prepared, incubated with anti-IKK-α antibody, and then immunoprecipitated using protein A/G-Sepharose beads. Immunocomplex kinase reaction was performed as described below. Whole-cell extracts were fractionated on 7.5% SDS-PAGE and immunoblotted using anti-IKK-α and anti-IKK-β antibodies.

FIG. 5C shows IKK phosphorylates p65 peptides in cell-free system. Whole-cell extracts were prepared from TNF-treated cells and immunoprecipitated with antibody against IKK-α. Thereafter immunocomplex kinase assay was performed in the presence of the peptides as a substrate.

FIG. 6B shows A293 cells were transiently transfected with a NF-κB-containing plasmid along with indicated plasmids and then incubated with 150 μM PTD-p65-P1. Cells were exposed to TNF, and supernatants of the culture medium were assayed for SEAP. Results are expressed as fold activity of the vector control.

FIG. 6C shows KBM-5 cells were incubated with 150 μM PTD-p65-P1 for 1 h and treated with 0.1 nM TNF for the indicated times. Nuclear and cytoplasmic extracts were prepared and then fractionated on 10% SDS-PAGE.

FIG. 7B shows $1 \times 10^5$ cells were pretreated with 100 μM protein transduction domain-p65-P1, and then incubated with 1 nM TNF for 16 hour. Cells were stained with Live/Dead assay reagent for 30 min, and then analyzed under a fluorescence microscope.

FIG. 7C shows $1 \times 10^5$ cells were pretreated with 100 μM PTD-p65-P1, and then incubated with 1 nM TNF for 16 h. Cells were fixed, stained with TUNEL assay reagent, and then analyzed under a fluorescence microscope.

FIG. 7D shows protein transduction domain-p65-P1 enhances chemotherapy-induced cytotoxicity. Five thousand cells were seeded in triplicate in 96-well plates. Cells were pretreated with 100 μM protein transduction domain-p65-P1 and then incubated with indicated concentrations of TNF or doxorubicin or cisplatin for 72 hr. Thereafter, cell viability was analyzed by the MTT method.

DETAILED DESCRIPTION OF THE INVENTION

Figures 1A, 1B:
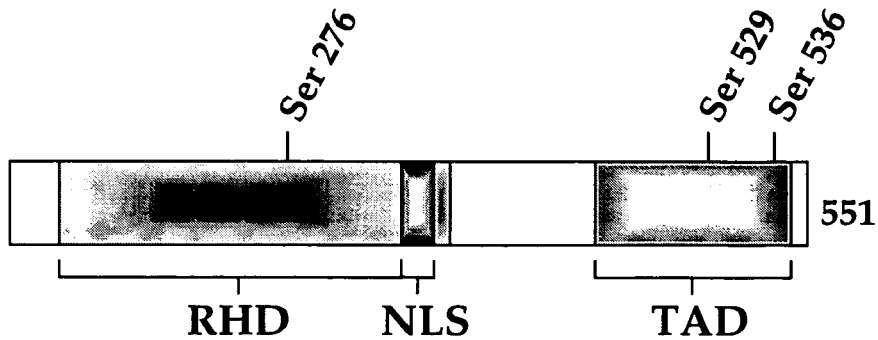
FIG. 1A-1B show the structure of the p65 subunit of NF-κB.

The following abbreviations are used herein: TNFR 1, TNF receptor 1; PIS, preimmune serum; IκB, inhibitory subunit of NF-κB; IKK, IκBα kinase; NIK, NF-κB-inducing kinase; TRAF 2, TNF receptor-associated factor-2; TRADD, TNF receptor-associated death domain; EMSA, electrophoretic mobility shift assay; SEAP, secretory alkaline phosphatase; IL-1, interleukin-1; PMA, phorbol myristate-acetate; SDS, sodium dodecyl sulfate; PAGE, polyacrylamide gel electrophoresis; ALLN, N-acetyl-leucyl-leucyl-norleucinal; PTD, protein transduction domain.

The nuclear transcription factor NF-κB has been shown to mediate inflammation, viral replication, carcinogenesis, anti-apoptosis, invasion and metastasis. Thus, specific inhibitors of this factor have therapeutic potential.

The present invention identifies NF-κB inhibitors that can suppress TNF-induced NF-κB activation in vivo. The NF-κB inhibitor was generated by linking a cell-delivery peptide to a polypeptide derived from the p65 subunit of NF-κB. More specifically, polypeptides which contain phosphorylation sites from the p65 subunit of NF-kB (e.g. SEQ ID NO. 5 or 11) were linked to the protein transduction domain peptides (SEQ ID NO. 3) derived from antennapedia third helix sequence. The resulting NF-κB inhibitors include protein transduction domain-p65-P1 (SEQ ID NO. 4, containing amino acid 271-282 of the p65 subunit) and protein transduction domain-p65-P6 (SEQ ID NO. 10, containing amino acid 525-537 of the p65 subunit).

Deletion of amino acids either from the C-terminus or the N-terminus of the p65-derived peptides abolished the NF-κB suppressive activity. Substitution of serine with alanine residue also abolished the inhibitory activity of the inhibitor. A concentration of 150 μM peptide is required to suppress NF-κB activation. Protein transduction domain-p65-P1 and protein transduction domain-p65-P6 inhibited TNF-induced NF-κB activation in vivo only when linked to the protein transduction domain peptide. Linkage to cell-permeable peptide was not required to suppress the binding of p50-65 to DNA in vitro.

Inhibitor PTD-p65-P1 had no effect on TNF-induced AP-1 activation, did not affect IkBα kinase (IKK) activation, IκBα phosphorylation or degradation, but did suppress p65 phosphorylation and nuclear translocation. Whether p65 phosphorylation is needed for nuclear translocation is not fully understood. It was also found that the polypeptide itself (p65-P1 and p65-P6) undergoes phosphorylation upon treatment with IKK. These results are consistent with previous reports which demonstrated IKK can induce phosphorylation of p65.

PTD-p65-P1 suppressed NF-kB activation induced by TNF, LPS, IL-1, okadaic acid, PMA, $H_2O_2$ or cigarette smoke condensate. These results indicate that the peptide inhibitor affects a common step in NF-kB activation.

PTD-p65-P1 also suppressed NF-kB regulated reporter gene expression induced by TNF, TNF receptor 1 (TNFR1), TNF receptor-associated death domain (TRADD), TNF receptor-associated factor 2 (TRAF2), NF-kB-inducing kinase (NIK), IKK and p65, and enhanced apoptosis induced by TNF and chemotherapeutic agents There are numerous reports which suggest that NF-κB mediates suppression of apoptosis. Several genes that are involved in suppression of apoptosis are regulated by NF-κB. These include cIAP, TRAF1, TRAF2, cFLIP, survivn, $bcl_{xl}$, and XIAP. It is possible that the polypeptide inhibitors of the present invention suppress the expression of these genes and thus potentiate apoptosis. Several genes that are involved in tumorigenesis, metastasis, angiogenesis and inflammation are also regulated by NF-kB. Thus, the polypeptide inhibitors reported herein have a potential in suppressing the synthesis of all these gene products and may have potential for therapeutic applications.

The present invention is directed to a cell permeable NF-κB inhibitor comprising (i) a peptide fragment of the p65 subunit of NF-κB, or homologues or derivatives thereof, and (ii) a protein transduction domain which is able to transport said peptide fragment across cell membrane. Preferably, the peptide fragment of the p65 subunit comprises phosphorylation site(s) of the p65 subunit of NF-κB. Examples of the p65 peptide fragments include peptides with the sequence of SEQ ID NO. 5 or 11. In general, the protein transduction domain is derived from the third helix of the antennapedia homeodomain, herpes virus structural protein, or HIV tat protein. In one embodiment of the present invention, the protein transduction domain derived from the third helix of the antennapedia homeodomain has the sequence of SEQ ID NO. 3. Representative examples of the NF-κB inhibitors include peptides with the sequence of SEQ ID NO. 4 or 10.

In another embodiment, the present invention provides methods of using the NF-κB inhibitor of the present invention to inhibit DNA binding activity of NF-κB or enhance apoptosis in a cell. In general, DNA binding activity of NF-κB induced by TNF, LPS, IL-1, okadaic acid, PMA, $H_2O_2$, cigarette smoke condensate, TNFR1, TRADD, TRAF2, NIK, or IKK could be inhibited by the inhibitor, whereas apoptosis induced by TNF, or chemotherapeutic agent such as doxorubicin or cisplatin could be enhanced by the inhibitor.

In yet another embodiment, the NF-κB inhibitor of the present invention can be used to treat cancer in an individual. It is well known in the art that NF-κB activation plays an important role in cancer development, and inhibition of NF-κB activities is generally believed to be beneficial in cancer treatment. Moreover, the NF-κB inhibitor disclosed herein can be used in combination with chemotherapeutic agent in the treatment of cancer.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Reagents and Cell Lines

Bacteria-derived human recombinant TNF, purified to homogeneity with a specific activity of $5 \times 10^7$ U/mg, was kindly provided by Genentech (South San Francisco, Calif.). Penicillin, streptomycin, Iscove's modified Dulbecco's medium, and FBS were obtained from Invitrogen (Carlsbad, Calif.). Lipopolysaccharide, PMA, okadaic acid, $H_2O_2$ and anti-β-actin antibody were obtained from Sigma Chemical (St. Louis, Mo.). The cigarette smoke condensate was provided by Dr. C. Gary Gariola (Univ. of Kentucky, Lexington, Ky.).

Polyclonal anti-p65, anti-p50, anti-IκBα, anti-cyclin D1 and anti-MMP-9 antibodies were obtained from Santa Cruz Biotechnology (Santa Cruz, Calif.). Phospho-specific anti-IκBα (Ser32) antibody was purchased from Cell Signaling (Beverly, Mass.). Phospho-specific anti-p65 antibody was kindly provided by Rockland Laboratory. Anti-IKK-α and anti-IKK-β antibodies were kindly provided by Imgenex (San Diego, Calif.). Anti-COX2 antibody was obtained from BD Biosciences Pharmingen (San Diego, Calif.).

All peptides (see FIG. 1) were synthesized using an automated peptide synthesizer (Symphony Multiplex, Rainin Instruments, MA). The peptides were purified to more than 90% purity using HPLC.

Leukemic cell line KBM-5 is phenotypically myeloid with monocytic differentiation. Cells were cultured in Iscove's modified Dulbecco's medium supplemented with 15% FBS, 100 U/ml penicillin, and 100 mg/ml streptomycin. A293 embryonic kidney cells were maintained in minimum essential medium supplemented with 10% FBS, with 100 U/ml penicillin, and 100 μg/ml streptomycin.

EXAMPLE 2

Electrophoretic Mobility Shift Assays

NF-κB activation was examined by electrophoretic mobility shift assays as described (Chaturvedi et al., 1994; Takada and Aggarwal). Briefly, nuclear extracts prepared from TNF-treated cells ($1 \times 10^6$/ml) were incubated with $^{32}$P-end-labeled 45-mer double-stranded NF-κB oligonucleotide (10 ug of protein with 16 fmol of DNA) from the human immunodeficiency virus long terminal repeat, 5'-TTGTTACAAGGGACTTTCCGCTGGGGACTTTC CAGGGAGGCGTGG-3' (SEQ ID NO. 1, boldface indicates NF-κB binding sites) for 30 min at 37° C., and the DNA-protein complex formed was separated from free oligonucleotide on 6.6% native polyacrylamide gels. A double-stranded mutated oligonucleotide, 5'-TTGTTA-CAACTCACTTTCCGCTGCTCACTTTC-CAGGGAGGCGTGG-3'(SEQ ID NO. 2) was used to examine the specificity of binding of NF-κB to the DNA. The specificity of binding was also examined by competition with unlabeled oligonucleotide.

For supershift assays, nuclear extracts prepared from TNF-treated cells were incubated with antibodies against either the p50 or p65 subunits of NF-κB for 30 min at 37° C. and then the complex was analyzed by electrophoretic mobility shift assays. Antibodies against cyclin D1 and preimmune serum (PIS) were included as negative controls. The dried gels were visualized, and radioactive bands quantitated by a PhosphorImager (Molecular Dynamics, Sunnyvale, Calif.) using Imagequant software.

EXAMPLE 3

IκKBα Kinase (IKK) Assay

The IKK assay was performed by a method described previously (Manna et al., 2000a). Briefly, IKK complex from whole-cell extract was precipitated with antibody against IKK-α, followed by treatment with protein A/G-Sepharose beads (Pierce, Rockford, Ill.). After a 2-h incubation, the beads were washed with lysis buffer and then assayed in kinase assay mixture containing 50 mM HEPES (pH 7.4), 20 mM MgCl$_2$, 2 mM dithiothreitol (DTT), 20 mCi [γ-$^{32}$P] ATP, 10 mM unlabeled ATP, and 2 μg of substrate GST-IκBα (1-54). After incubation at 30° C. for 30 min, the reaction was terminated by boiling with SDS sample buffer for 5 min. Finally, the protein was resolved on 10% SDS-PAGE, the gel was dried, and the radioactive bands were visualized by PhosphorImager.

To determine the total amounts of IKK-α and IKK-β in each sample, 30 mg of the whole-cell protein was resolved on 7.5% SDS-PAGE, electrotransferred to a nitrocellulose membrane, and then blotted with either anti-IKK-α or anti-IKK-β antibodies. Cell-free phosphorylation of peptide by IKK was also determined using 10 μg of peptides as a substrate in the kinase reaction mixture described above, and then fractionated on 20% SDS-PAGE in 2×SDS electrophoresis buffer.

EXAMPLE 4

NF-κB-Dependent Reporter Secretory Alkaline Phosphatase (SEAP) Expression Assay

The effect of the inhibitory peptides on TNF-, TNFR-, TRADD-, TRAF 2-, NIK-, IKK, and p65-induced NF-κB-dependent reporter gene transcription was analyzed by SEAP assay as previously described (Manna et al., 2000b). Briefly, A293 cells ($5 \times 10^5$ cells/well) were plated in 6-well plates and transiently transfected by calcium phosphate method with pNF-kB-SEAP (0.5 μg). To examine TNF-induced reporter gene expression, the cells were transfected with 0.5 μg of SEAP expression plasmid and 2 μg of control plasmid pCMVFLAG1 DNA for 24 hours. Thereafter the cells were treated for 24 hours with 150 μM peptides, and then stimulated with 1 nM TNF for 24 hours. The cell culture medium was then harvested and analyzed for alkaline phosphatase (SEAP) activity according to the protocol essentially as described by the manufacturer (Clontech, Palo Alto, Calif.) using a 96-well fluorescence plate reader (Fluoroscan II, Labsystems, Chicago, Ill.) with excitation set at 360 nm and emission at 460 nm.

EXAMPLE 5

Cytotoxicity Assay (MTT Assay)

The cytotoxic effects of LPS were determined by the MTT uptake method as described (Manna et al., 2000a). Briefly, 5000 cells were incubated with synthetic peptides for 1 hour in triplicate in 96-well plates, and then treated with various concentration of TNF for 72 hours at 37° C. Thereafter, MTT solution was added to each well. After a 2-hr incubation at 37° C., extraction buffer (20% SDS, 50% dimethylformamide) was added, the cells were incubated overnight at 37° C., and then the OD was measured at 570 nm using a 96-well multiscanner (Dynex Technologies, MRX Revelation; Chantilly, Va.).

The cytotoxic effects of TNF were determined by the Live/Dead assay. Briefly, $1 \times 10^5$ cells were incubated with 100 μM PTD-p65-P1 for 1 h, and then treated with 1 nM TNF for 16 hr at 37° C. Cells were stained with Live/Dead reagent (5 μM ethidium homodimer, 5 μM calcein-AM), and then incubated at 37° C. for 30 min. Cells were analyzed under a fluorescence microscope (Labophot-2, Nikon, Tokyo, Japan).

EXAMPLE 6

TUNEL Assay

The TNF-induced apoptosis was determined by TUNEL assay using In Situ Cell Death Detection reagent (Roche Applied Science). Briefly, $1 \times 10^5$ cells were incubated with PTD-p65-P1 for 1 h, and then treated with 1 nM TNF for 16 hr at 37° C. Thereafter, cells were plated on a poly 1-lysine-coated glass slide by centrifugation using a cytospin 4

(Thermoshendon, Pittsburg, Pa.), air-dried, fixed with 4% paraformaldehyde, and permeabilized with 0.1% of Triton-X 100 in 0.1% sodium citrate. After washing, the cells were incubated with reaction mixture for 60 min at 37° C. Stained cells were mounted with mounting medium purchased from Sigma Chemicals and analyzed under a fluorescence microscope (Labophot-2).

EXAMPLE 7

Cell Permeable Peptides Derived from p65 Subunit of NF-κB Inhibits TNF-Induced NF-κB Activation The p65 subunit of NF-κB was targeted to design polypeptides that suppress NF-κB activation. The p65 consists of a DNA-binding and dimerization domain (RHD), a nuclear localization domain (NLS), and a transactivation domain (TD). The phosphorylation residue Ser 276 present in the DNA-binding and dimerization domain, and residues Ser 529 and Ser 536 in the transactivation domain were targeted (see FIG. 1A). Polypeptides derived from the p65 subunit were linked to the protein transduction domain (PTD) derived from the third helix of the antennapedia homeodomain (FIG. 1B). These polypeptides were then tested for its ability to suppress NF-κB activation induced by various proinflammatory stimuli.

Figure 3A:
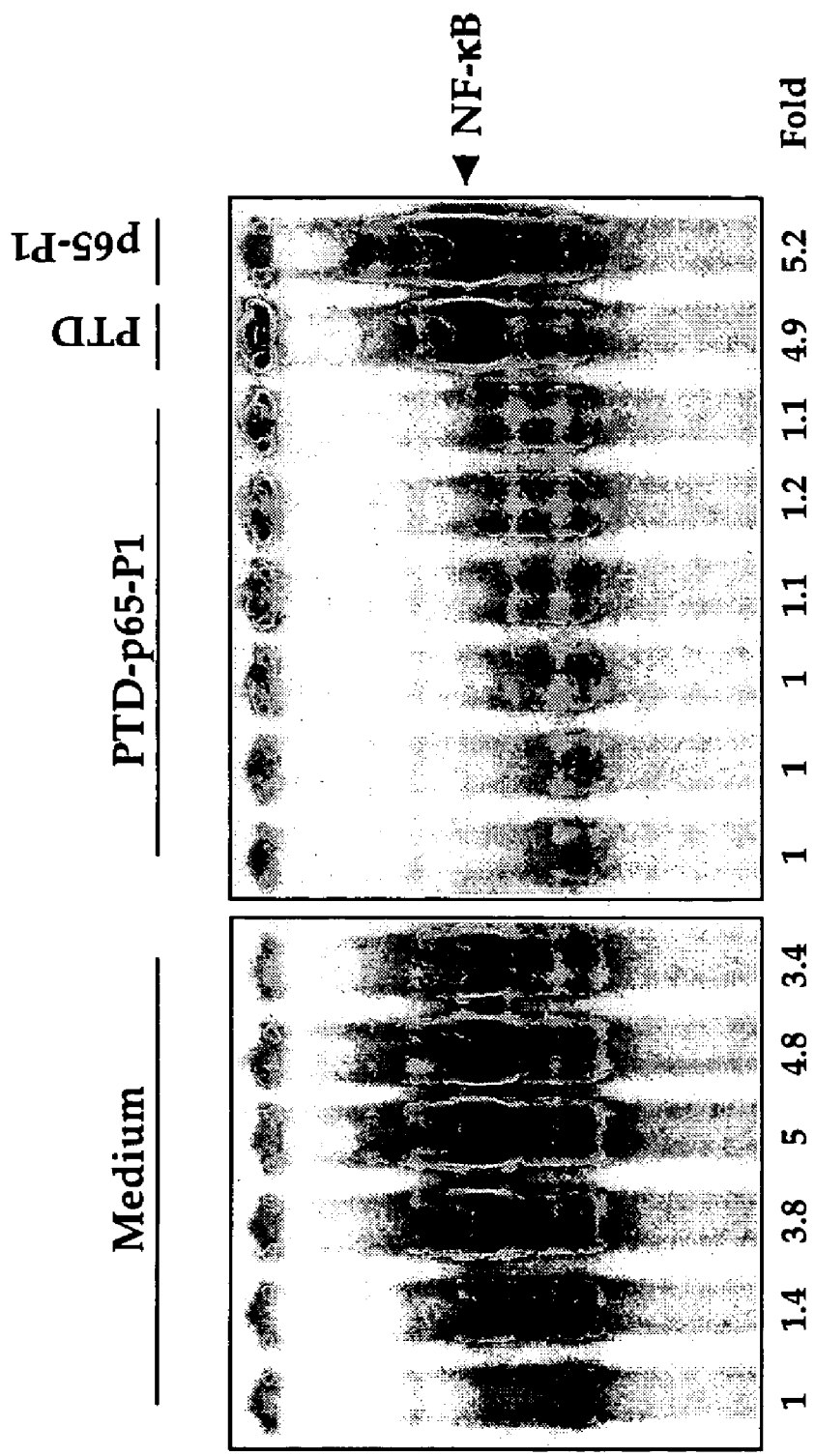
FIGS. 3A-3D shows PTD-p65-P1 polypeptide inhibits TNF-induced NF-κB activation.
Figure 3B:
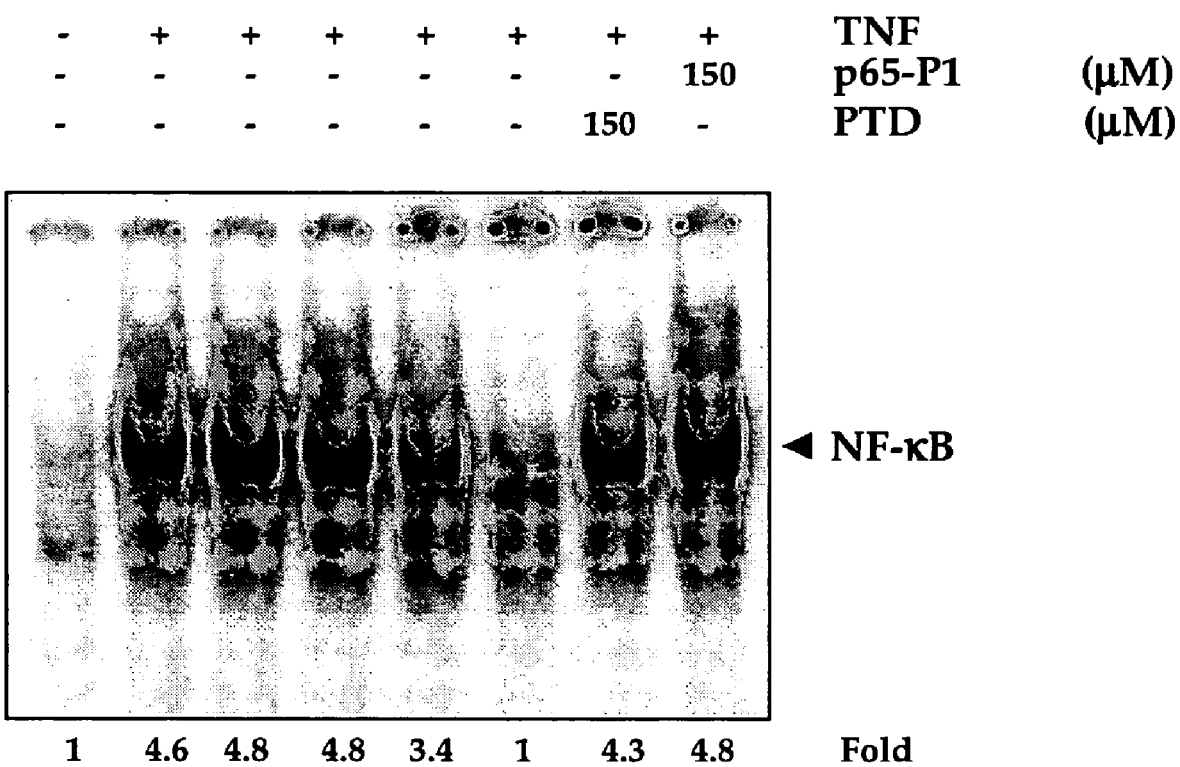

To determine the effects of peptide containing Ser 276 (PTD-p65-P1), KBM-5 cells was preincubated with the peptides for 1 h, and then treated with 0.1 nM TNF for the indicated times. Nuclear extracts were prepared, and NF-κB activation was analyzed by electrophoretic mobility shift assays (EMSA). TNF-induced NF-κB activation in a time dependent manner and pretreatment with PTD-p65-P1 completely abolished the TNF-induced NF-κB activation (FIG. 3A). Neither a protein transduction domain nor p65-P1 alone had any effect on TNF-induced NF-κB activation, indicating that p65-P1 must be attached to a protein transduction domain for it to enter the cells. Minimum dose of PTD-p65-P1 required to suppress NF-κB activation was also investigated. PTD-p65-P1 suppressed TNF-induced NF-κB activation by 25% at 100 μM and completely at 150 μM (FIG. 3B).

Figure 3C:
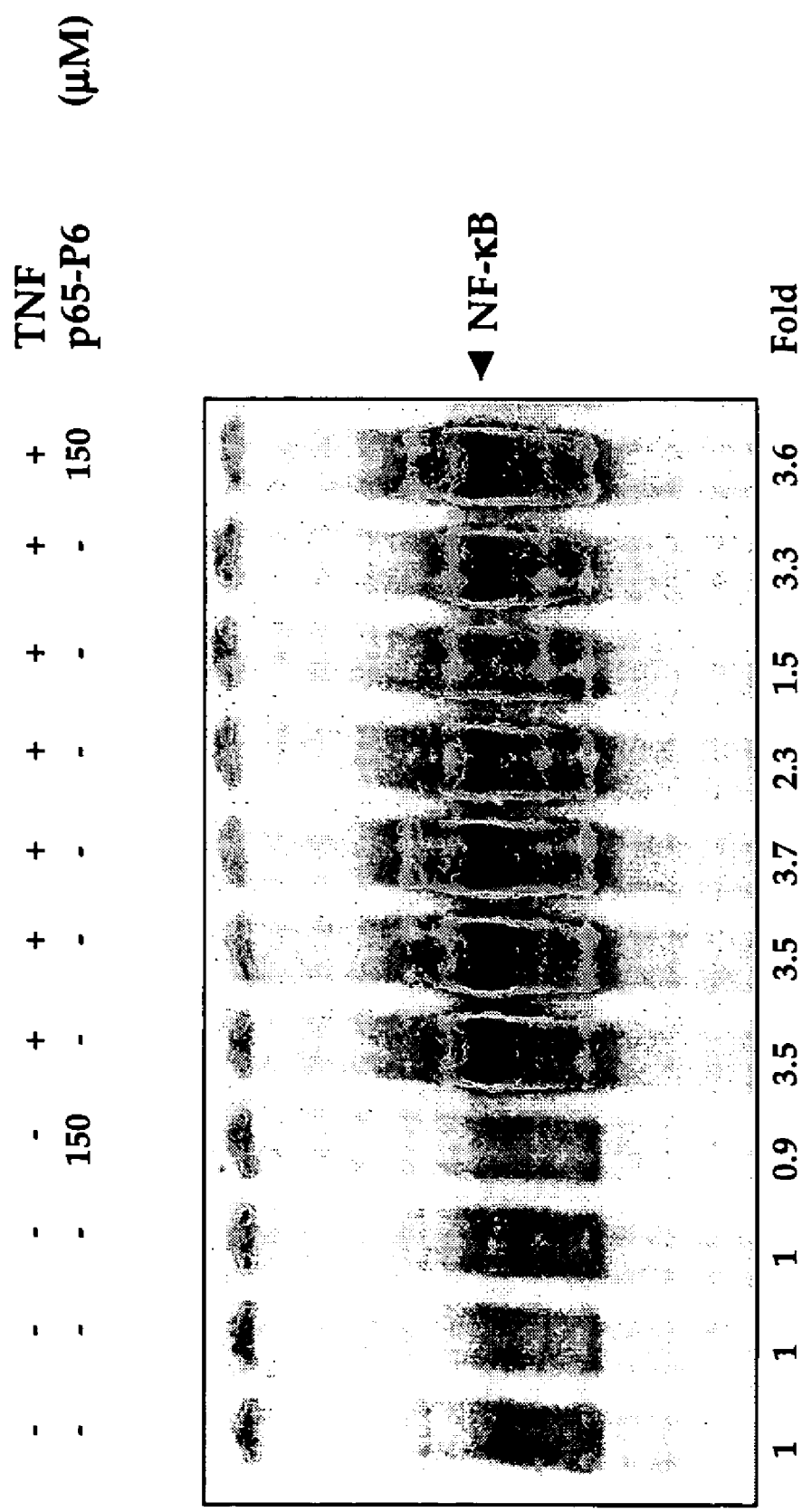

To determine the effects of peptide containing Ser 529 and 536 (PTD-p65-P6), KBM-5 cells were preincubated with various concentrations of peptides for 1 h and then treated with 0.1 nM TNF for 30 min. PTD-p65-P6 inhibited TNF-induced NF-κB activation in a dose dependent manner. Neither a protein transduction domain nor p65-P6 alone had any effect on TNF-induced NF-κB activation (FIG. 3C).

EXAMPLE 8

Specific Amino Acid Sequence Required for Suppression of NF-κB Activation

Figure 2A:
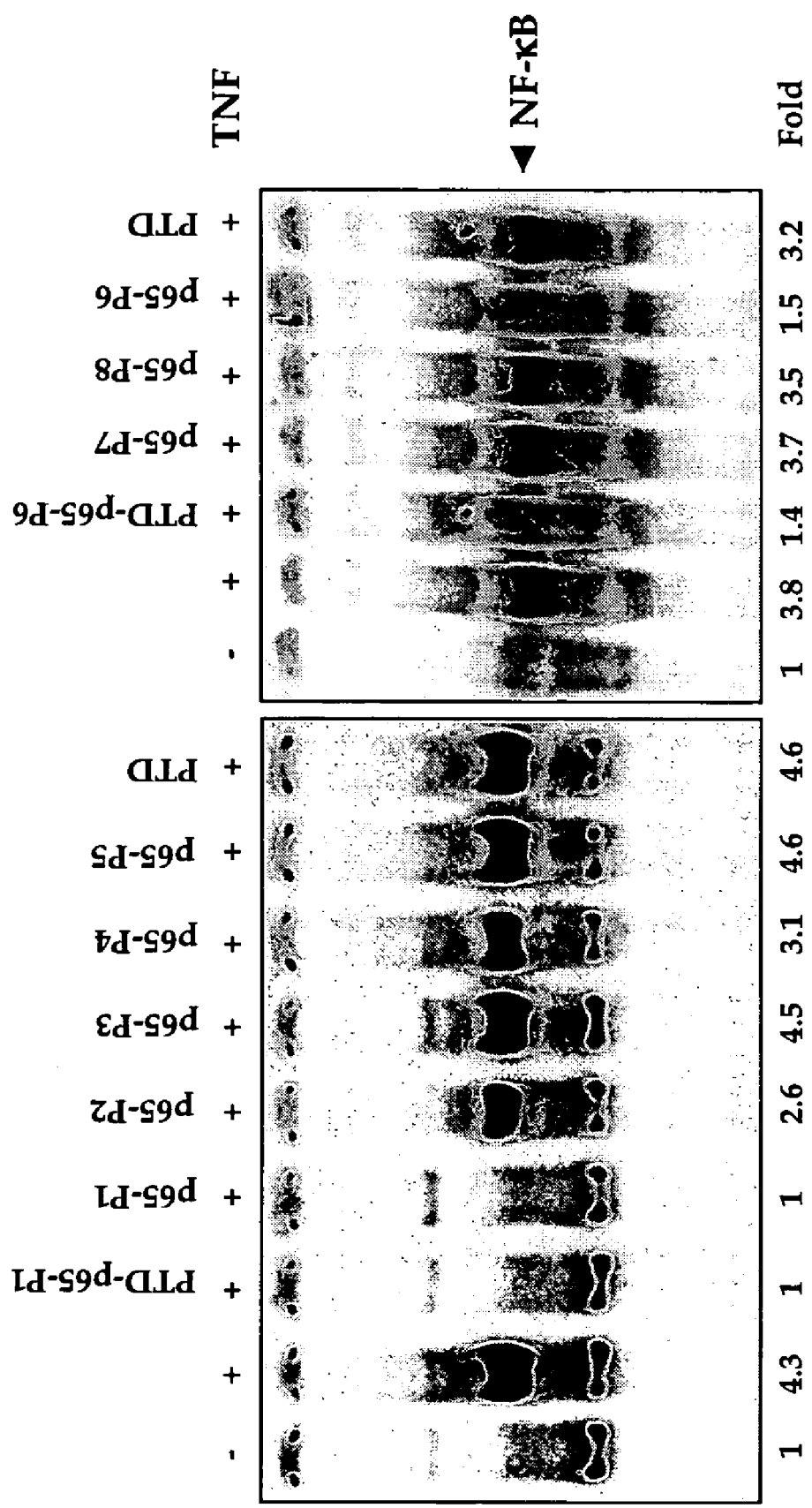
FIGS. 2A-2B shows the effect of various peptides containing the phosphorylation site of p65 on NF-κB activation.

The above in vitro assay was used to determine amino acid sequence required for NF-κB inhibition (FIG. 2A). Peptide in which Ser 276 was mutated (p65-P2) did not inhibit NF-κB binding to the DNA. Peptides in which five amino acid residues were deleted from the C-terminus (p65-P4) or three amino acid residues were deleted from the N-terminus (p65-P5) were also inactive. The minimum peptide required for suppression of NF-κB activation was QLRRPSDRELSE (p65-P1, SEQ ID NO. 5).

Whether p65-P6 can suppress p50-p65 binding to DNA was examined. Peptide in which Ser 529 was mutated (p65-P7) or Ser 536 was mutated (p65-p8) did not inhibit NF-κB binding to DNA (FIG. 2A). These results suggest that the inhibition of TNF-induced NF-κB activation by p65-P6 requires the presence of both phosphorylation sites, Ser529 and 536. In contrast, p65-$P_1$ contains single phosphorylation site and it is needed to inhibit NF-κB activity. All subsequent studies were performed with protein transduction domain-p65-P1.

Figure 2B:
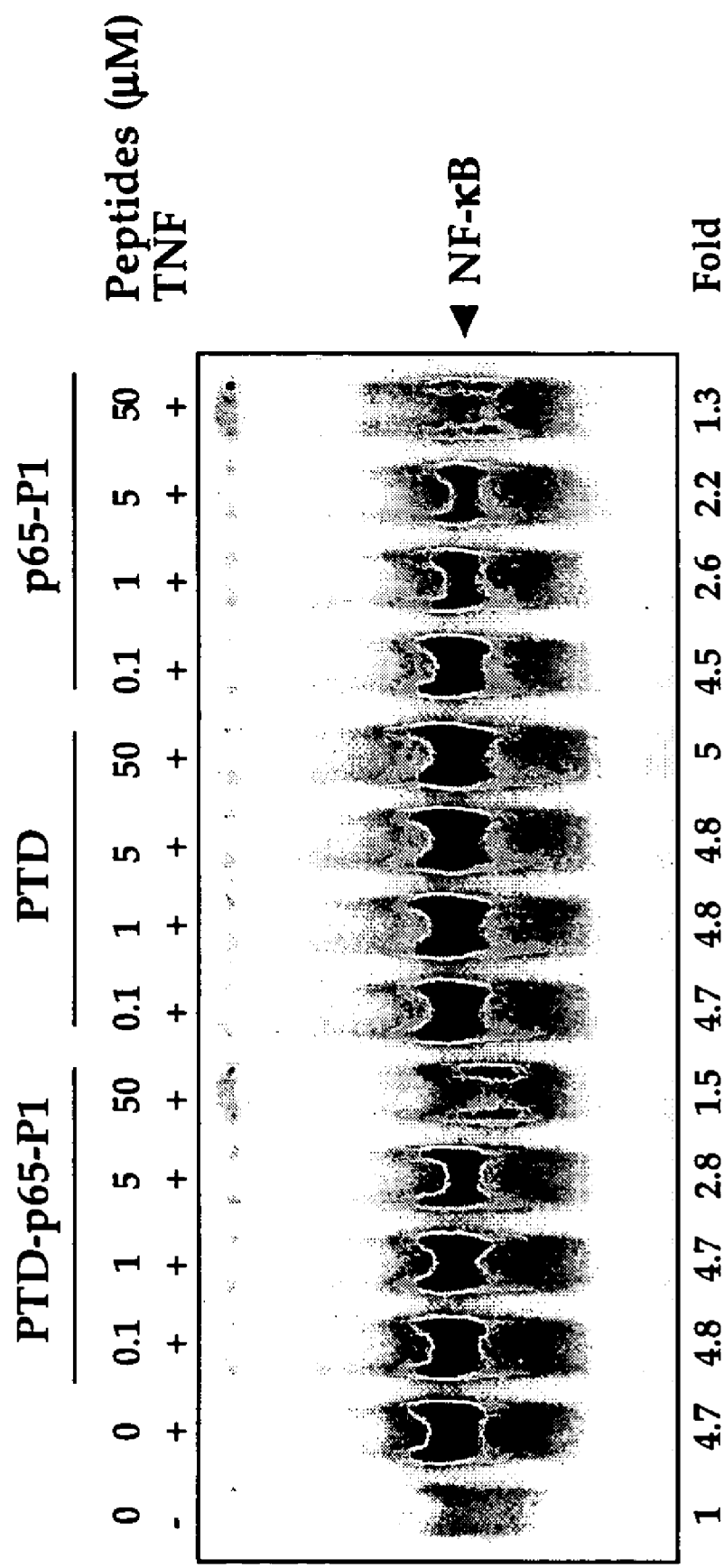

The dose-dependent effect of protein transduction domain-p65-P1 and p65-P1 on p50-p65 binding to DNA was investigated. Nuclear extracts from TNF-treated cells were incubated with different concentrations of the peptide and then examined for DNA binding. p65-P1 inhibited NF-κB binding in a dose-dependent manner, and maximum inhibition occurred at 50 μM (FIG. 2B). PTD-p65-P1 also inhibited NF-κB binding at the same concentration. The protein transduction domain alone had no effect.

EXAMPLE 9

Specificity of NF-κB Inhibition By PTD-p65-P1

Figure 3D:
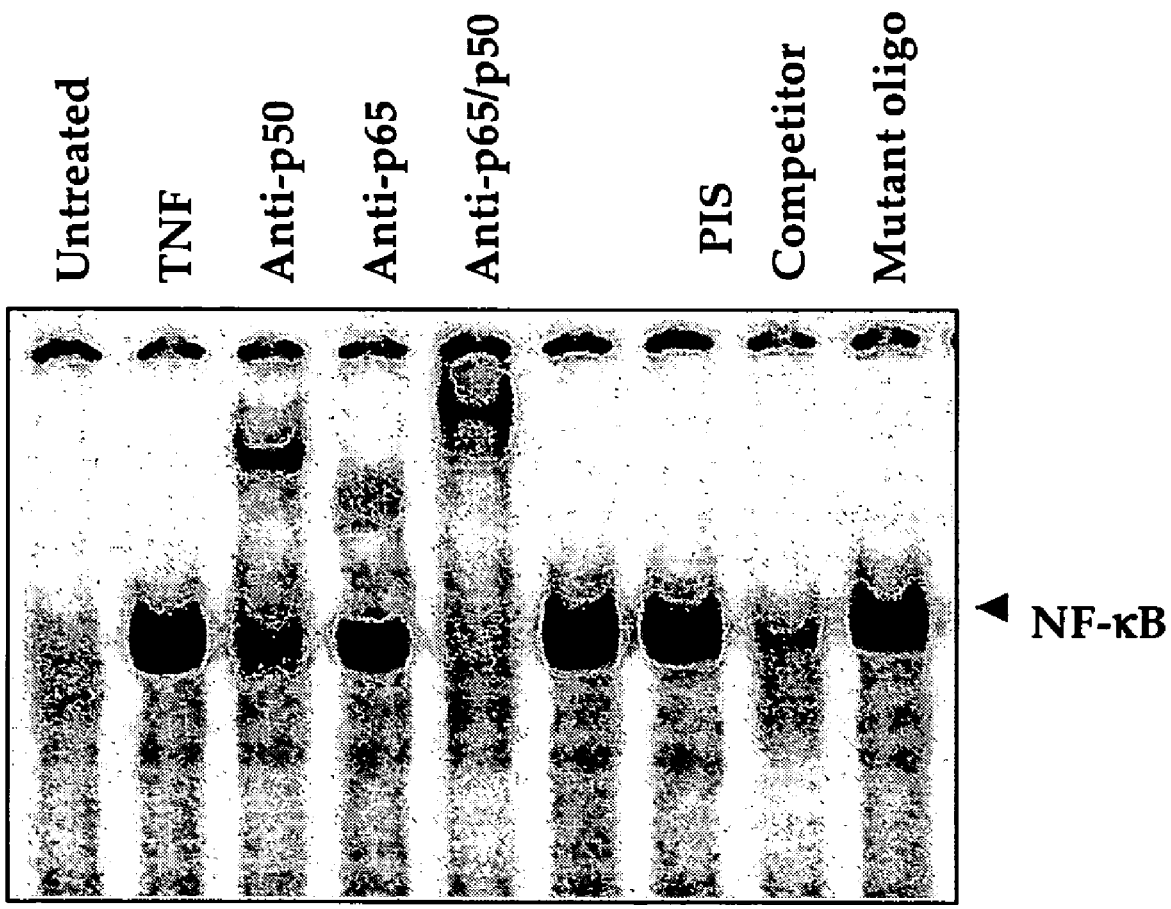

Since NF-κB is a complex of proteins, various combinations of Rel/NF-κB protein can constitute an active NF-κB heterodimer that binds to a specific sequence in the DNA. To show that the retarded band visualized by EMSA in TNF-treated cells was indeed NF-κB, nuclear extracts from TNF-stimulated cells were incubated with antibodies to either the p50 (NF-κB1) or the p65 (RelA) subunit of NF-κB. Both shifted the band to a higher molecular mass (FIG. 3D), suggesting that the TNF-activated complex consisted of p50 and p65 subunits. Neither preimmune serum (PIS) nor the irrelevant antibody anti-cyclin D1 had any effect. Excess unlabeled NF-κB (100-fold; competitor) caused complete disappearance of the band, but not by mutant oligonucleotide (Mutant oligo).

EXAMPLE 10

TNF-Induced AP-1 Activation is not Inhibited by PTD-p65-P1

Figure 4A:
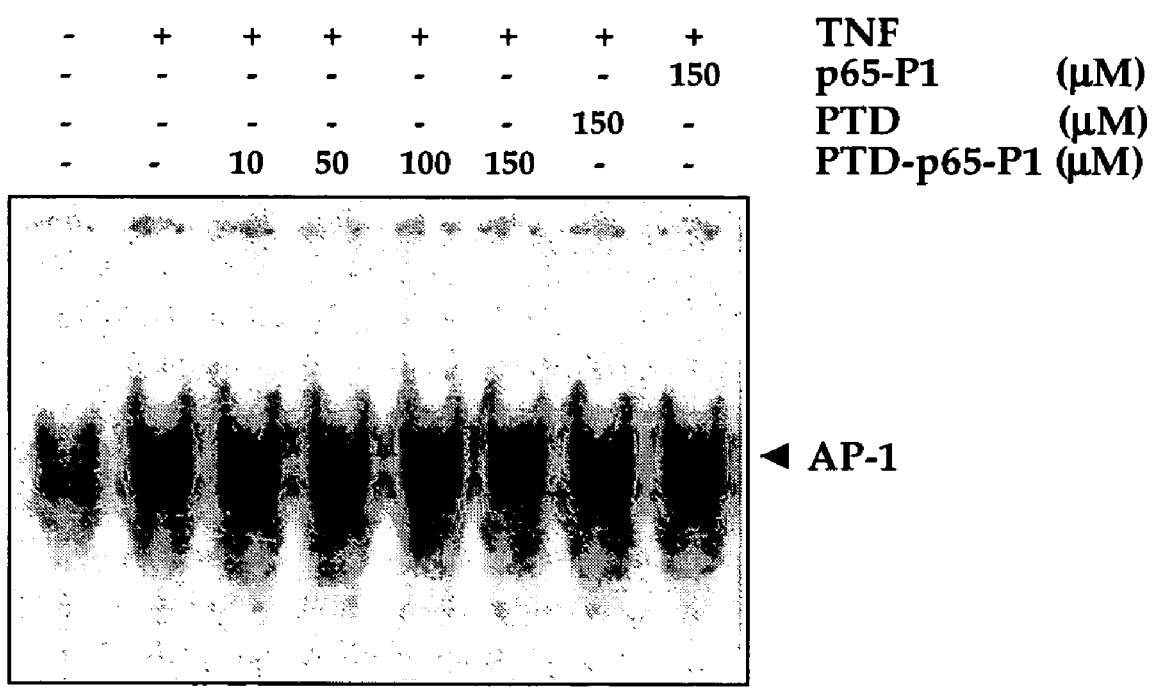

Like NF-κB, TNF is also a potent activator of AP-1. Whether PTD-p65-P1 affects TNF-induced AP-1 activation was therefore investigated. To determine this, cells were treated with 0.1 nM TNF for the indicated times, nuclear extracts were prepared and assayed for AP-1 activation by EMSA (FIG. 4A). TNF activated AP-1, but protein transduction domain-p65-P1 had no effect on the activation of AP-1.

EXAMPLE 11

PTD-p65-P1 Inhibits NF-κB Activation Induced by Different Activiators

Lipopolysaccharide, IL-1, okadaic acid, PMA, $H_2O_2$, and cigarette smoke condensate are potent activators of NF-κB, but the mechanisms differ. The inventors examined whether PTD-p65-P1 could suppress NF-κB activated by these agents. Cells were preincubated with 150 μM protein transduction domain-p65-P1 for 1 h, treated with 0.1 nM TNF, 1 μg/ml LPS, 100 ng/ml IL-1, 500 nM okadaic acid, 10 ng/ml PMA, 500 μM $H_2O_2$, or 1 μg/ml cigarette smoke condensate and then analyzed for NF-κB activation by EMSA. PTD-p65-P1 suppressed the activation of NF-κB induced by all these agents (FIG. 4B), suggesting that the PTD-p65-P1 acts at a step common to all these agents.

EXAMPLE 12

PTD-p65-P1 has no Effect on IκBα Phosphorylation or Degradation

Figure 5A:
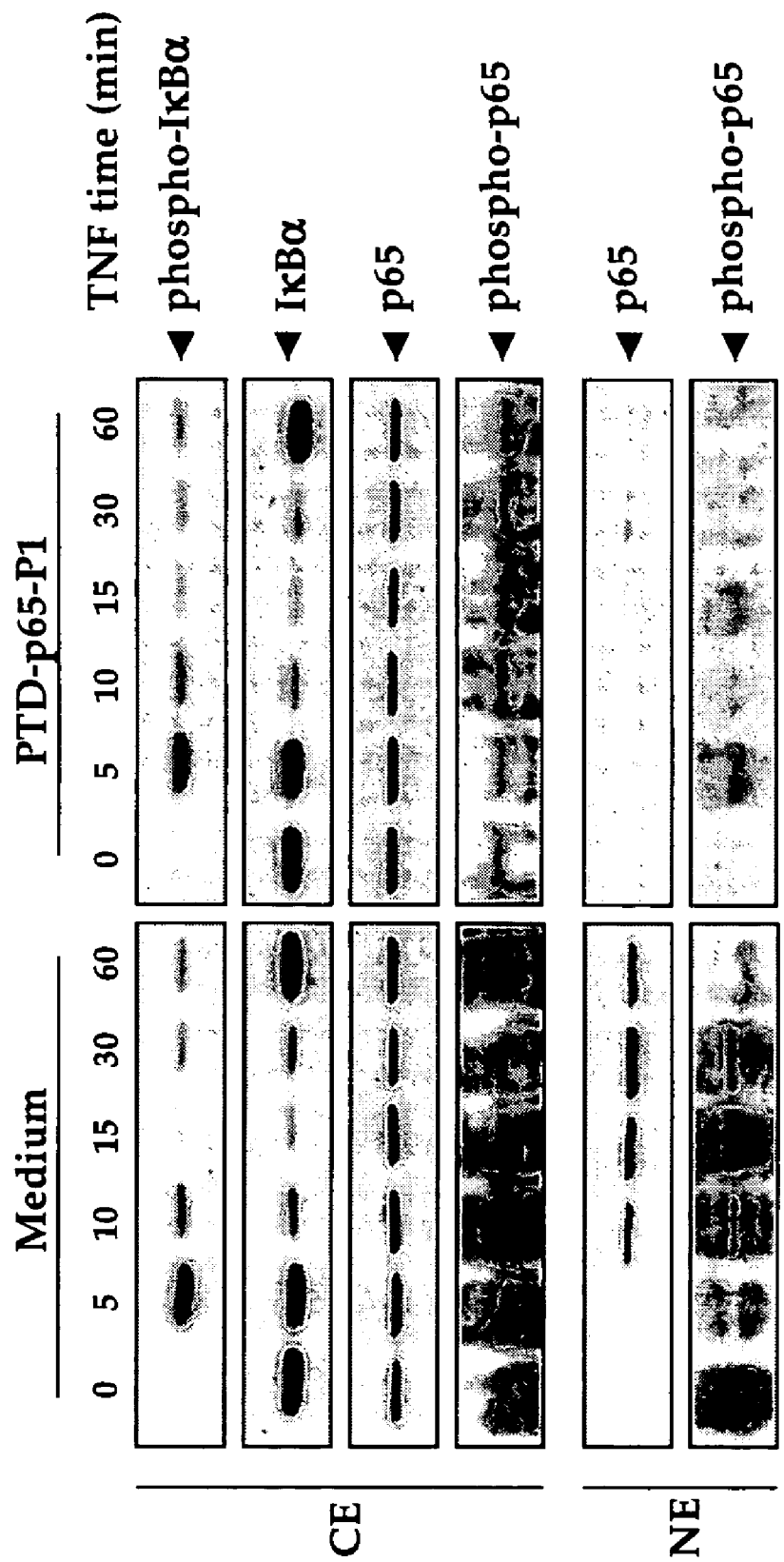
FIGS. 5A-5C shows PTD-p65-P1 has no effect on the TNF-induced IκBα phosphorylation or degradation, but inhibits p65 phosphorylation and nuclear translocation. Cells were incubated with 150 μM PTD-p65-P1 for 1 h and treated with 0.1 nM TNF for the indicated times. Nuclear and cytoplasmic extracts were prepared and then fractionated on 10% SDS-PAGE. Western blot analysis was performed using with phospho-specific anti-IκBα, anti-IκBα, phospho-specific anti-p65, anti-p65, and β-actin.

The translocation of NF-κB to the nucleus is preceded by the phosphorylation, ubiquitination, and proteolytic degradation of IκBα. To determine whether PTD-p65-P1 inhibits TNF-induced NF-κB activation by inhibition of IκBα degradation and phosphorylation, cells were pretreated with the polypeptide for 1 h, and then exposed to 0.1 nM TNF for the indicated times. IκBα status in the cytoplasm was examined by Western blot analysis. As shown in FIG. 5A, pretreatment of cells with protein transduction domain-p65-P1 had no effect on either TNF-induced phosphorylation or degradation of IκBα.

EXAMPLE 13

PTD-p65-P1 Inhibits p65 Phosphorylation and Nuclear Translocation

The effect of PTD-p65-P1 on TNF-induced phosphorylation and nuclear translocation of p65 was also analyzed. Western blot analysis showed that TNF induced nuclear translocation of p65 in a time-dependent manner. As early as 5 min after TNF stimulation, p65 was translocated to the nucleus, and remained constant till 30 min (FIG. 5A, middle panel). The results also show that TNF induced phosphorylation of p65 in a time-dependent manner, whereas protein transduction domain-p65-P1 suppressed it almost completely (FIG. 5A, bottom). These results suggest that protein transduction domain-p65-P1 suppressed TNF-induced NF-κB activation by inhibiting phosphorylation and nuclear translocation of p65.

EXAMPLE 14

PTD-p65-P1 has no Effect on TNF-Induced IKK Activation

Figure 5B:
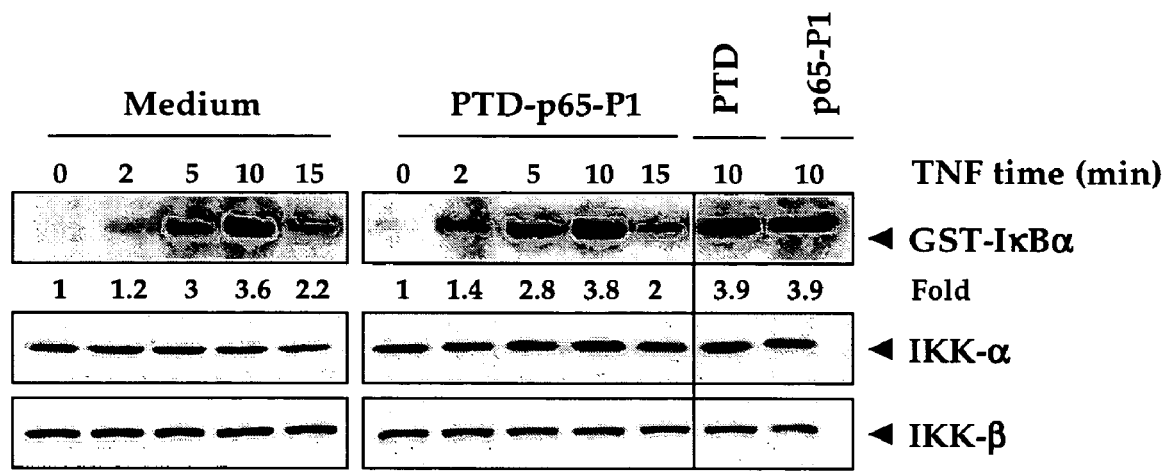

Since IKK is required for TNF-induced NF-κB activation, the effect of protein transduction domain-p65-P1 on TNF-induced IKK activation was determined next. Immune complex kinase assays showed that TNF activated IKK as early as 5 min after TNF treatment, and protein transduction domain-p65-P1 had no effect on this activation (FIG. 5B).

EXAMPLE 15

Figure 5C:
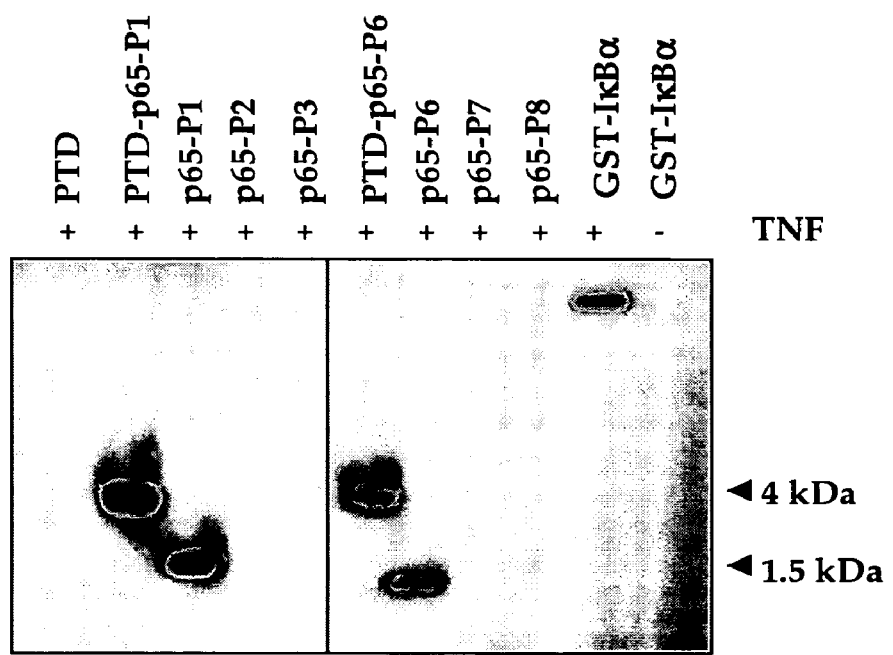

IKK Phosphorylates p65-Peptides in Cell-Free System p65-P1 and p65-p6 have one or two serine residues respectively. Whether these serine residues can be phosphorylated by IKK was investigated. Whole-cell extracts from TNF-treated cells were immunoprecipitated with antibody against IKK and then immunocomplex kinase assay was performed using p65-peptides as substrates. After reaction, samples were fractionated on 20% SDS-PAGE with 2-fold electrophoresis buffer. FIG. 5C shows that precipitated IKK complex can phosphorylate p65-P1 and p65-p6, indicating that synthetic peptides from the p65 subunit of NF-κB can be phosphorylated by IKK complex. The results also showed that p65-peptides in which Ser 276, 529 or 536 were mutated into alanine did not undergo phosphorylation by the IKK complex, indicating that Ser 276, 529 and 536 are necessary for p65 to be phosphorylated by IKK.

EXAMPLE 16

PTD-p65-P1 Inhibits TNF-Induced NF-κB-Dependent Reporter Gene Expression

Although electrophoretic mobility shift assays show that protein transduction domain-p65-P1 blocks NF-κB activation, DNA binding does not always correlate with NF-κB-dependent gene transcription, suggesting there are additional regulatory steps. To determine the effect of protein transduction domain-p65-P1 on TNF-induced NF-κB-dependent reporter gene expression, cells were transiently transfected with the NF-κB-regulated SEAP reporter construct. The cells were incubated with the polypeptide, and then stimulated with TNF.

Figure 6A:
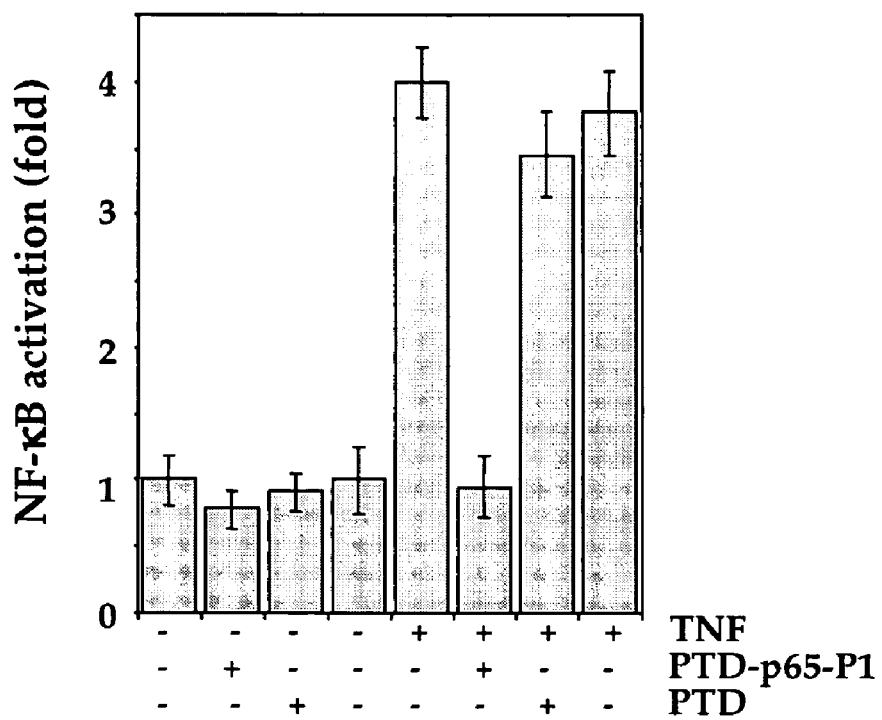
FIGS. 6A-6C shows PTD-p65-P1 inhibits TNF-induced expression of NF-κB-dependent gene. A293 cells were transiently transfected with NF-κB-containing plasmid linked to the SEAP gene and incubated with 150 μM PTD-p65-P1. Cells were treated with 1 nM TNF, and supernatants were collected and assayed for SEAP.

An almost 4-fold increase in SEAP activity over vector control was observed upon stimulation with TNF. Polypeptide protein transduction domain-p65-P1 completely suppressed the TNF-induced stimulation, but protein transduction domain or p65P1 alone failed to suppress it (FIG. 6A). These results demonstrate that PTD-p65-P1 also represses NF-κB-dependent reporter gene expression induced by TNF.

TNF-induced NF-κB activation is mediated through sequential interaction of the TNF receptor with TRADD, TRAF 2, NIK, and IKK, resulting in phosphorylation of IκBα. To delineate the site of action of PTD-p65P1 in the TNF-signaling pathway leading to NF-κB activation, cells were transfected with TNFR 1-, TRADD-, TRAF 2-, NIK-, IKK-, and p65-expressing plasmids and then monitored for NF-κB-dependent SEAP expression. As shown in FIG. 6B, all of the plasmid transfected cells induced NF-κB-SEAP gene expression, and protein transduction domain-p65P1 suppressed NF-κB reporter gene expression induced by all. These results suggest that protein transduction domain-p65P1 affects NF-κB activation at a terminal step.

EXAMPLE 17

PTD-p65-P1 Inhibits TNF-Induced NF-κB-Dependent Cyclin D1, COX2 and MMP-9 Gene Expression TNF-treatment induces expression of cyclin D1, COX-2 and MMP-9 which have NF-κB binding sites in their promoters. The investigators next examined whether protein transduction domain-p65-P1 inhibits TNF-induced cyclin D1, COX-2 and MMP-9. Cells were pretreated with PTD-p65-P1 for 1 h, then treated with TNF for the indicated times, and whole-cell extracts were prepared and analyzed by Western blot analysis for the expression of cyclin D1, COX-2 and MMP-9.

Figure 6C:
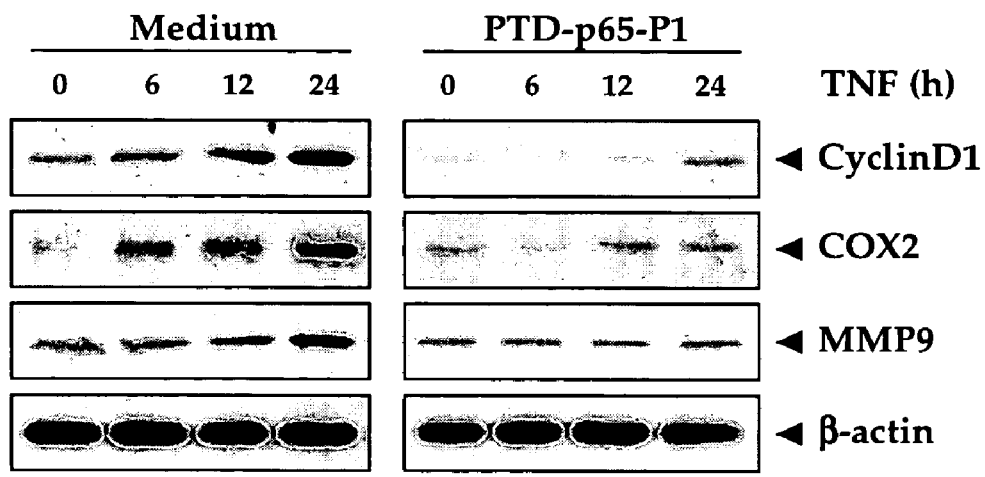
Figure 6B:
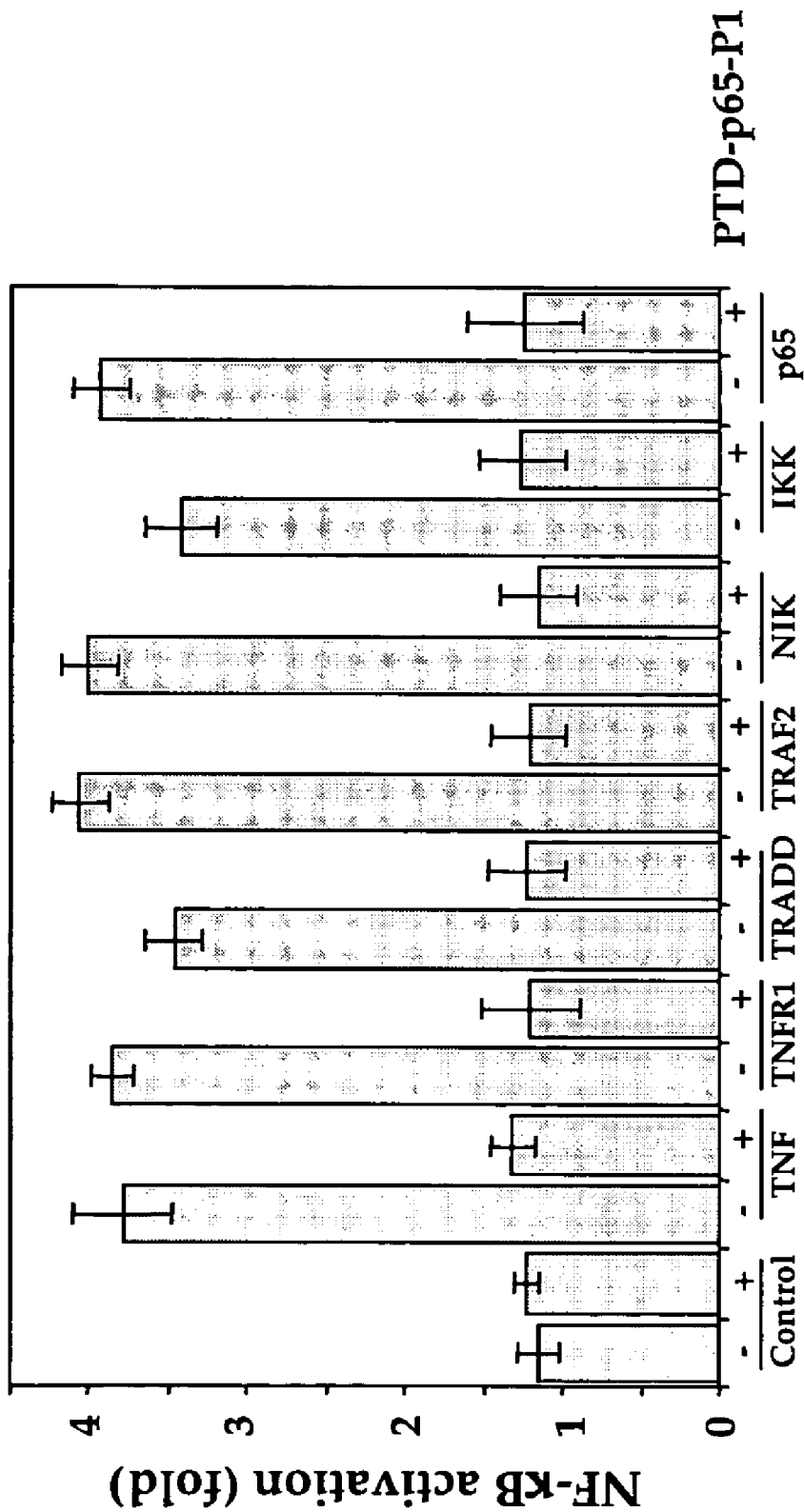

As shown in FIG. 6C, TNF induced Cyclin D1, COX-2 and MMP-9 expressions in a time-dependent manner. PTD-p65-P1 blocked TNF-induced expression of these gene products.

EXAMPLE 18

PTD-p65-P1 Enhances TNF-Induced Cytotoxicity

Activation of NF-κB has been shown to inhibit TNF-induced apoptosis, whereas suppression of NF-κB stimulates TNF-induced apoptosis. Whether suppression of NF-κB by protein transduction domain-p65P1 affects TNF-induced cytotoxicity was investigated by MTT assay.

Figure 7A:
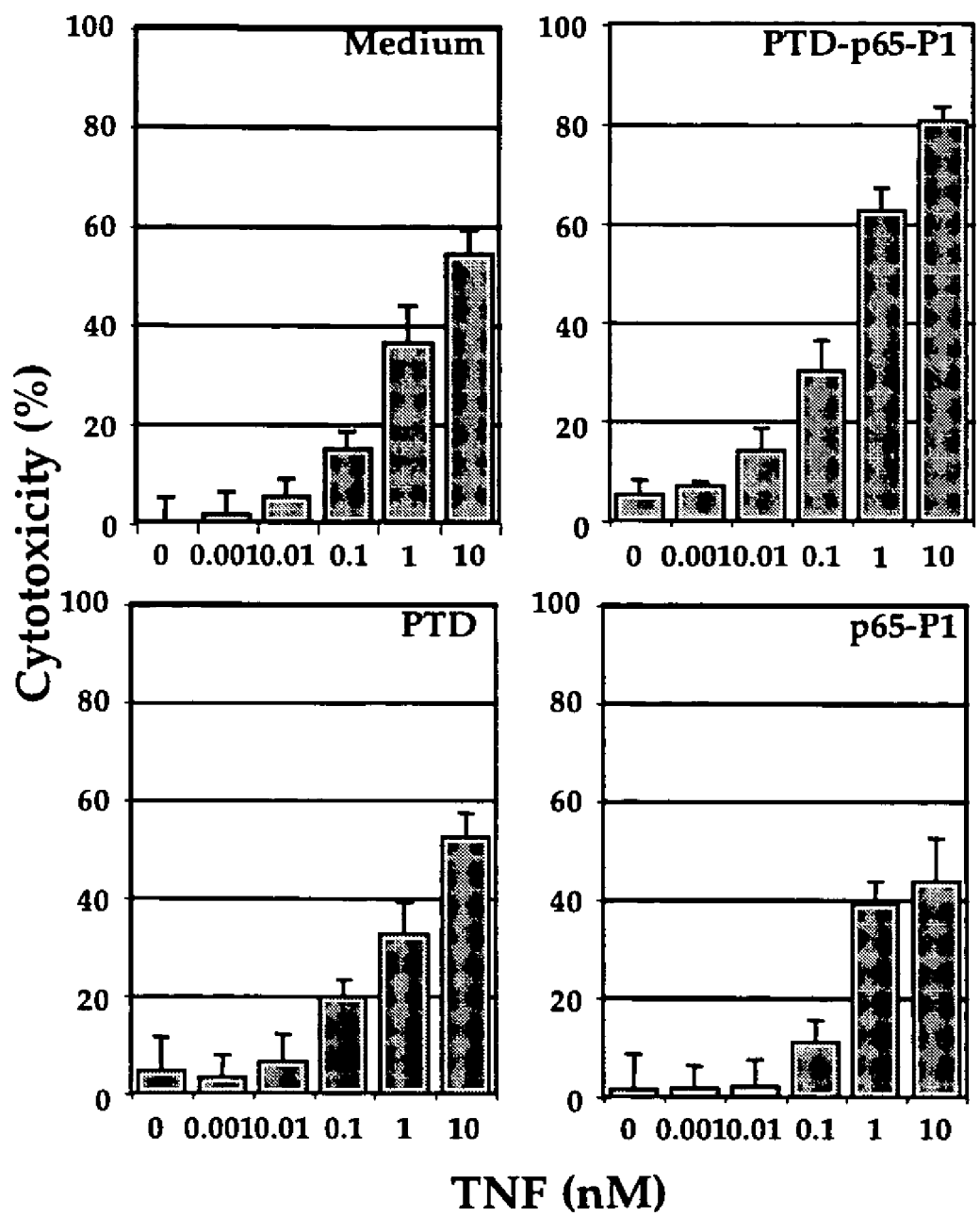
FIGS. 7A-7D shows protein transduction domain-p65-P1 enhances TNF-induced cytotoxicity. Five thousand KBM-5 cells were seeded in triplicate in 96-well plates. Cells were pretreated with 100 μM PTD-p65-P1, and then incubated with the indicated concentrations of TNF for 72 hour. Thereafter, cell viability was analyzed by MTT assay.

As shown in FIG. 7A, TNF was cytotoxic to KBM-5 cells and protein transduction domain-p65P1 enhanced TNF-induced cytotoxicity. PTD or p65P1 by alone had no effect on TNF-induced cytotoxicity.

Figure 7B:
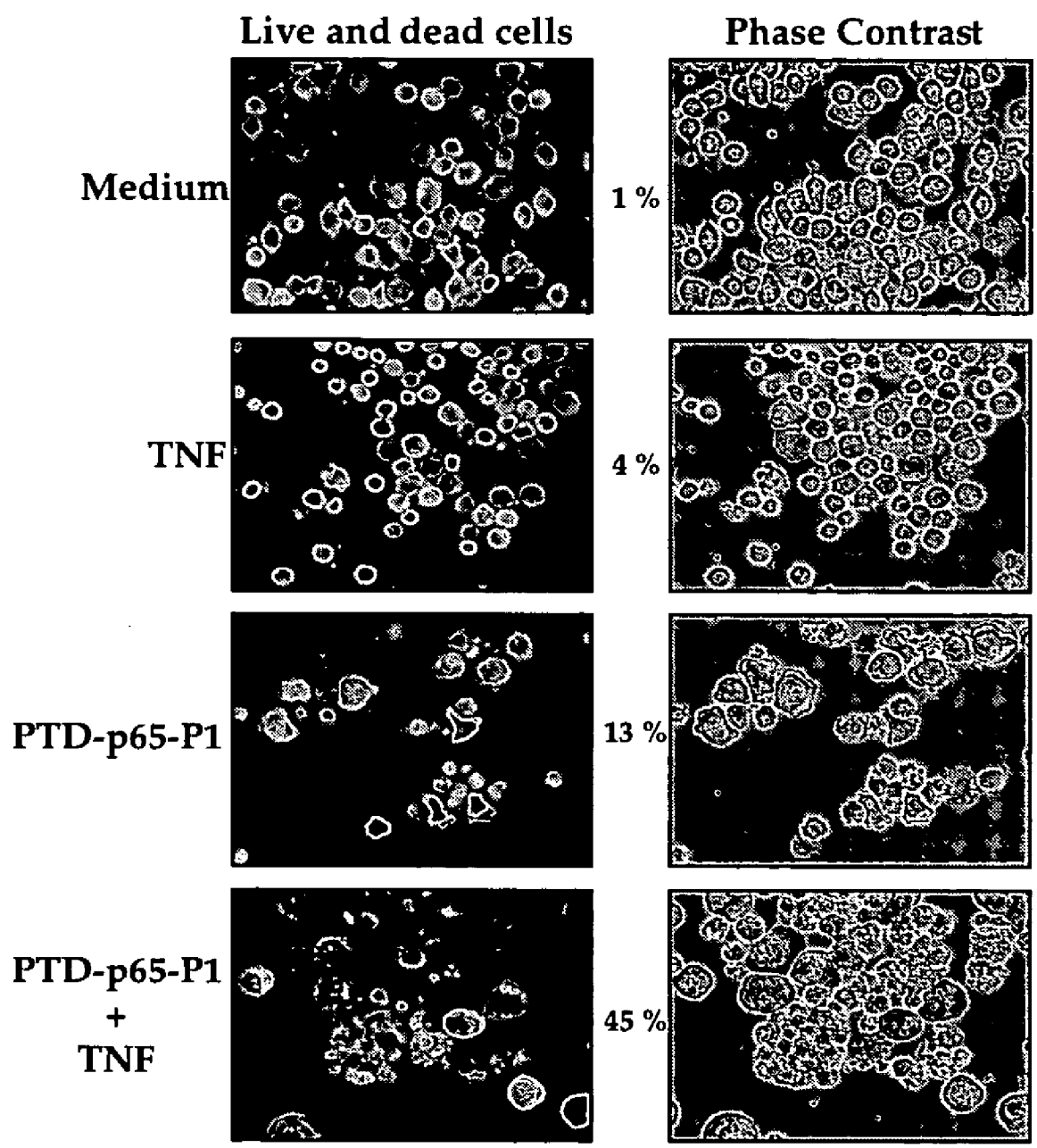
Figure 7C:
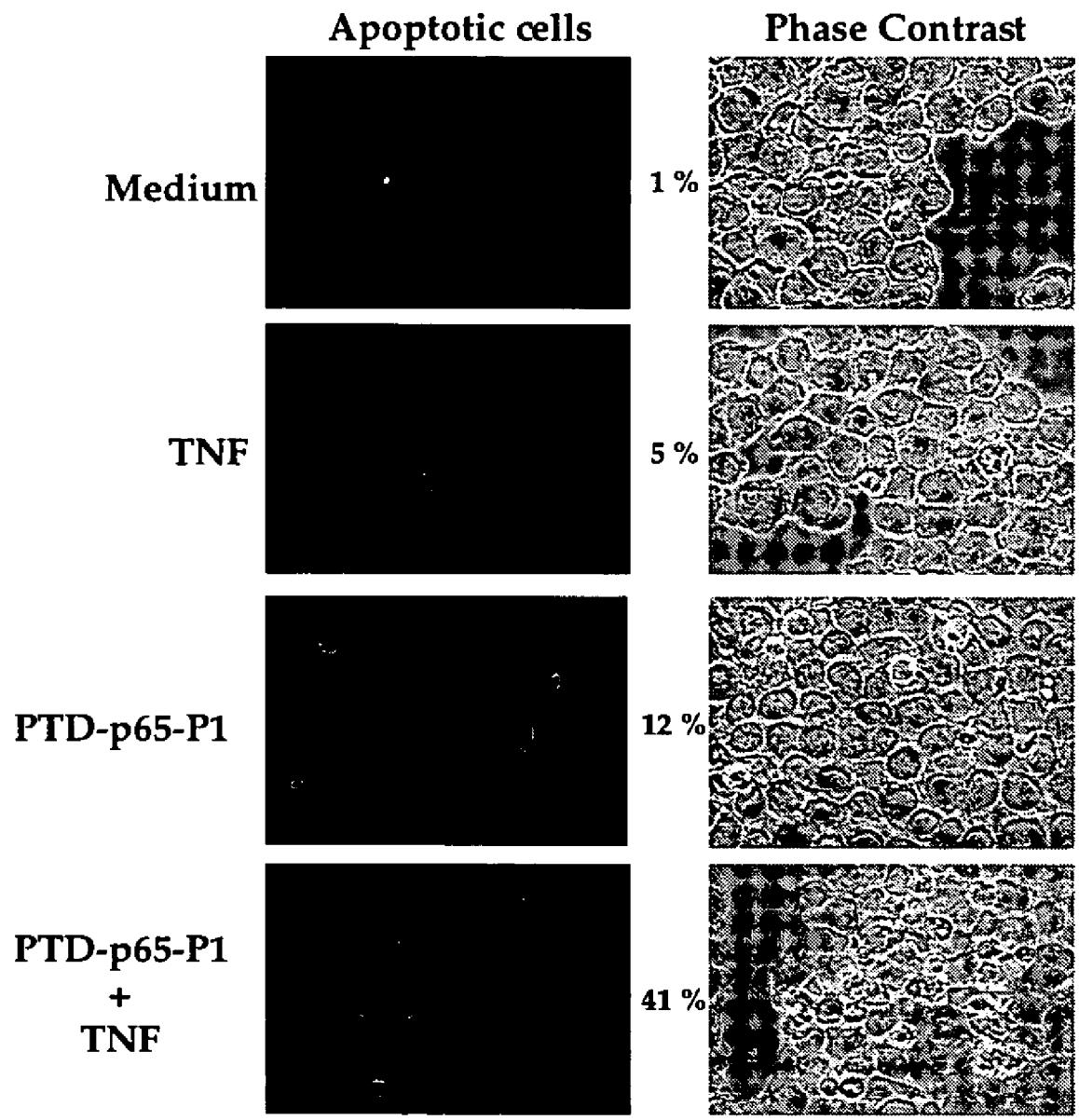

Whether suppression of NF-κB by protein transduction domain-p65-P1 affects TNF-induced apoptosis was also investigated by live and dead assay (FIG. 7B) and annexin V staining (FIG. 7C). These results show that TNF induced apoptosis in KBM-5 cells and PTD-p65P1 enhanced TNF-induced apoptosis from 4% to 45% (see red staining in FIG. 7B).

EXAMPLE 19

PTD-p65P1 Potentiates Chemotherapy-Induced Cytotoxicity

Chemotherapeutic agents are known to activate NF-κB and mediate chemoresistance. Whether suppression of NF-κB by PTD-p65-P1 affects chemotherapy-induced cytotoxicity was investigated by the MTT assay.

Figure 7D:
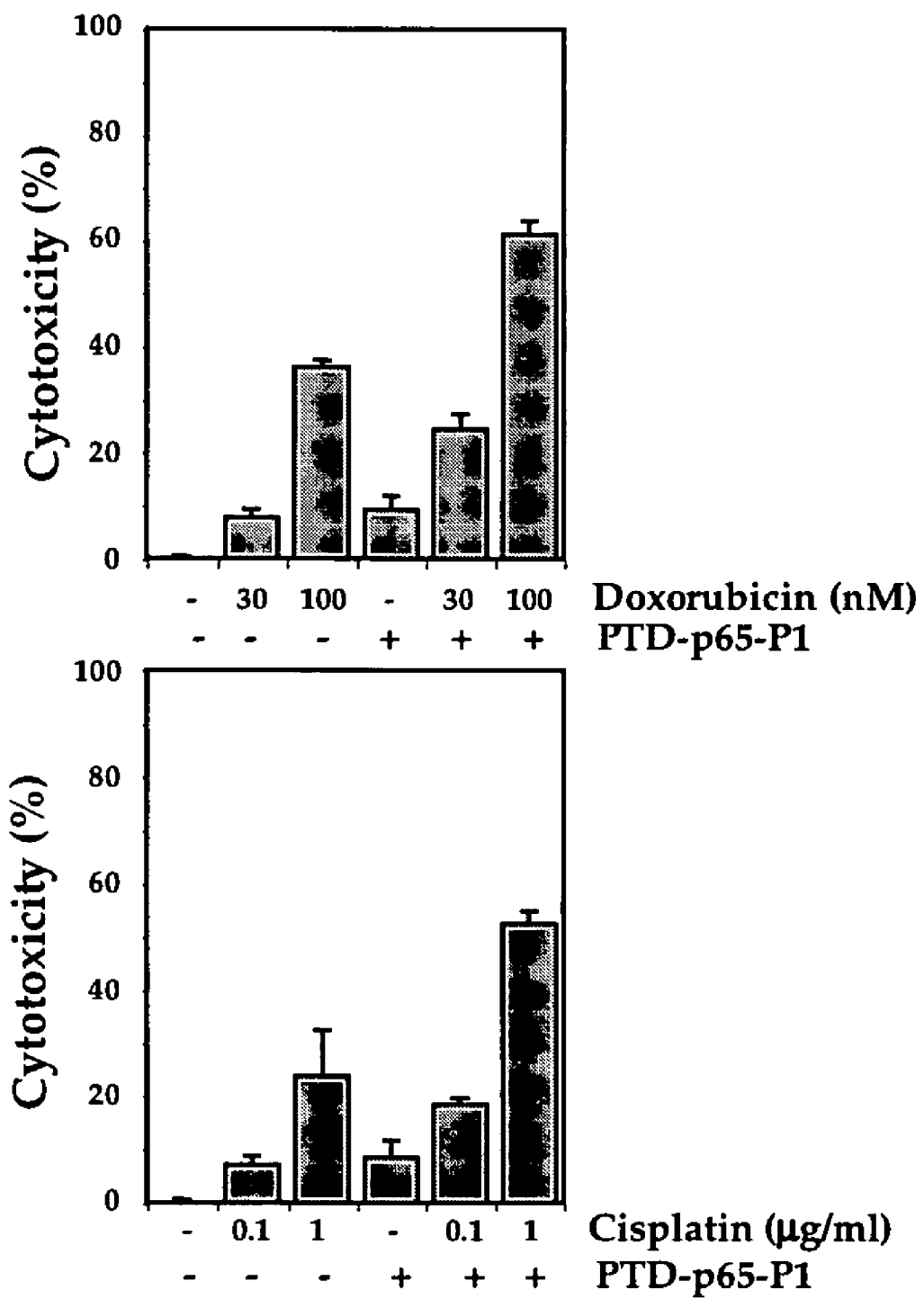

As shown in FIG. 7D, cytotoxicity induced by doxorubicin (top panel) and cisplatin (bottom panel) was potentiated by protein transduction domain-p65P1. These results suggest that protein transduction domain-p65-P1 has a therapeutic potential in combining with chemotherapy.

The following references were cited herein:

Chaturvedi et al., J Biol Chem. 269:14575-14583 (1994).
Derossi et al., J Biol Chem. 269:10444-10450 (1994).
Elliott and O'Hare, Cell 88:223-233 (1997).
Fawell et al., Proc Natl Acad Sci USA. 91:664-668 (1994).
Futaki et al., Curr Protein Pept Sci. 4:87-96 (2003).
Lindgren et al., Trends Pharmacol. Sci. 21:99-103 (2000).
Manna et al., J. Immunol. 165:4927-34 (2000a).
Manna et al., Cancer Res. 60:3838-47 (2000b).
Schwarze and Dowdy, Trends Pharmacol Sci. 21:45-48 (2000).
Takada and Aggarwal, J Biol Chem. 278:23390-23397.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A cell permeable NF-κB inhibitor polypeptide comprising:
   (i) a sequence selected from the group consisting of SEQ ID NO:5, SEQ ID NO:6, SEQ ID NO:7, SEQ ID NO:8, SEQ ID NO:9, SEQ ID NO:11, SEQ ID NO:12, and SEQ ID NO:13; and
   (ii) a transduction sequence selected from the group consisting of SEQ ID NO:3, a herpes virus structural protein transduction sequence, and HIV tat protein.

2. A cell permeable NF-κB inhibitor polypeptide having the amino acid sequence of SEQ ID NO. 4 or 10.

3. A composition comprising the inhibitor of claim 1 and a pharmacological acceptable carrier.

4. A polypeptide of the p65 subunit of NF-κB, wherein said polypeptide can inhibit NF-κB activity when said polypeptide is delivered into a cell, and said polypeptide comprises a sequence selected from the group consisting of SEQ ID NO:6, SEQ ID NO:7, SEQ ID NO:12, and SEQ ID NO:13.

5. The inhibitor of claim 1, wherein the transduction sequence is SEQ ID NO:3.

6. The inhibitor of claim 1, consisting of:
   (i) a sequence selected from the group consisting of SEQ ID NO:5, SEQ ID NO:6, SEQ ID NO:7, SEQ ID NO:8, SEQ ID NO:9, SEQ ID NO:11, SEQ ID NO:12, and SEQ ID NO:13; and
   (ii) a transduction sequence selected from the group consisting of SEQ ID NO:3, a herpes virus structural protein transduction sequence, and HIV tat protein.

7. The inhibitor of claim 6, wherein the transduction sequence is SEQ ID NO:3.

8. The inhibitor of claim 1, comprising SEQ ID NO:5.

9. The inhibitor of claim 1, comprising SEQ ID NO:6.

10. The inhibitor of claim 1, comprising SEQ ID NO:7.

11. The inhibitor of claim 1, comprising SEQ ID NO:8.

12. The inhibitor of claim 1, comprising SEQ ID NO:9.

13. The inhibitor of claim 1, comprising SEQ ID NO:11.

14. The inhibitor of claim 1, comprising SEQ ID NO:12.

15. The inhibitor of claim 1, comprising SEQ ID NO:13.

16. The inhibitor of claim 1, wherein the transduction sequence is SEQ ID NO:3.

17. The inhibitor of claim 1, wherein the transduction sequence is a herpes virus structural protein transduction sequence.

18. The inhibitor of claim 1, wherein the transduction sequence is an HIV tat protein.

19. The inhibitor of claim 2, having the amino acid sequence of SEQ ID NO.4.

20. The inhibitor of claim 2, having the amino acid sequence of SEQ ID NO:10.

21. The polypeptide of claim 4, wherein the polypeptide comprises SEQ ID NO:6.

22. The polypeptide of claim 4, wherein the polypeptide comprises SEQ ID NO:7.

23. The polypeptide of claim 4, wherein the polypeptide comprises SEQ ID NO:12.

24. The polypeptide of claim 4, wherein the polypeptide comprises SEQ ID NO:13.

25. The inhibitor of claim 6, consisting of SEQ ID NO:5 and a transduction sequence selected from the group consisting of SEQ ID NO:3, a herpes virus structural protein transduction sequence, and HIV tat protein.

26. The inhibitor of claim 6, consisting of SEQ ID NO:6 and a transduction sequence selected from the group consisting of SEQ ID NO:3, a herpes virus structural protein transduction sequence, and HIV tat protein.

27. The inhibitor of claim 6, consisting of SEQ ID NO:7 and a transduction sequence selected from the group consisting of SEQ ID NO:3, a herpes virus structural protein transduction sequence, and HIV tat protein.

28. The inhibitor of claim 6, consisting of SEQ ID NO:8 and a transduction sequence selected from the group consisting of SEQ ID NO:3, a herpes virus structural protein transduction sequence, and HIV tat protein.

29. The inhibitor of claim 6, consisting of SEQ ID NO:9 and a transduction sequence selected from the group consisting of SEQ ID NO:3, a herpes virus structural protein transduction sequence, and HIV tat protein.

30. The inhibitor of claim 6, consisting of SEQ ID NO:11 and a transduction sequence selected from the group consisting of SEQ ID NO:3, a herpes virus structural protein transduction sequence, and HIV tat protein.

31. The inhibitor of claim 6, consisting of SEQ ID NO:12 and a transduction sequence selected from the group consisting of SEQ ID NO:3, a herpes virus structural protein transduction sequence, and HIV tat protein.

32. The inhibitor of claim 6, consisting of SEQ ID NO:13 and a transduction sequence selected from the group consisting of SEQ ID NO:3, a herpes virus structural protein transduction sequence, and HIV tat protein.

33. The inhibitor of claim 6, wherein the transduction sequence consists of SEQ ID NO:3.

34. The inhibitor of claim 6, wherein the transduction sequence consists of a herpes virus structural protein transduction sequence.

35. The inhibitor of claim 6, wherein the transduction sequence consists of an HIV tat protein.

* * * * *